US009839668B2

(12) United States Patent
Poglitsch et al.

(10) Patent No.: US 9,839,668 B2
(45) Date of Patent: Dec. 12, 2017

(54) COMPOSITIONS AND METHODS FOR THE TREATMENT OF DISEASES RELATED TO THE RENIN-ANGIOTENSIN-SYSTEM

(71) Applicant: ATTOQUANT DIAGNOSTICS GMBH, Vienna (AT)

(72) Inventors: Marko Poglitsch, Vienna (AT); Cornelia Schwager, Vienna (AT); Hans Loibner, Vienna (AT)

(73) Assignee: ATTOQUANT DIAGNOSTICS GMBH, Vienna (AT)

( * ) Notice: Subject to any disclaimer, the term of this patent is extended or adjusted under 35 U.S.C. 154(b) by 0 days.

(21) Appl. No.: 15/103,618

(22) PCT Filed: Dec. 11, 2014

(86) PCT No.: PCT/EP2014/077452
§ 371 (c)(1),
(2) Date: Jun. 10, 2016

(87) PCT Pub. No.: WO2015/086774
PCT Pub. Date: Jun. 18, 2015

(65) Prior Publication Data
US 2016/0310562 A1    Oct. 27, 2016

(30) Foreign Application Priority Data
Dec. 11, 2013  (EP) ................................... 13196740
Jan. 9, 2014   (EP) ................................... 14150608

(51) Int. Cl.
| | |
|---|---|
| A61K 31/40 | (2006.01) |
| A61K 38/16 | (2006.01) |
| A61K 45/06 | (2006.01) |
| A61K 31/401 | (2006.01) |
| A61K 38/48 | (2006.01) |
| A61K 9/00 | (2006.01) |

(52) U.S. Cl.
CPC .......... *A61K 38/164* (2013.01); *A61K 9/0053* (2013.01); *A61K 31/401* (2013.01); *A61K 38/4813* (2013.01); *A61K 45/06* (2013.01)

(58) Field of Classification Search
CPC .................................................... A61K 31/40
USPC ........................................................ 514/423
See application file for complete search history.

(56) References Cited

PUBLICATIONS

Chaikuad et al., "Structure of human aspartyl aminopeptidase complexed with substrate analogue: insight into catalytic mechanism, substrate specificity and M18 peptidase family", *BMC Structural Biology*, 12(1): 14, 2012.
Fournie-Zaluski et al., "Brain renin-angiotensin system blockade by systemically active aminopeptidase A inhibitors: a potential treatment of salt-dependent hypertension", *Proceedings of the National Academy of Sciences of the United States of America*, 101(20): 7775-7780, 2004.
International Search Report and Written Opinion issued in PCT/EP2014/077452, dated Apr. 22, 2015.
Kitamura et al., "Effects of aminopeptidase P inhibition on kinin-mediated vasodepressor responses", *American Journal of Physiology*, 276(5): H1664-H1671, 1999.
Leckie, "Targeting the Renin-angiotensin System: What's new?", *Current Medicinal Chemistry—Cardiovascular and Hematological Agents*, 3(1): 23-32, 2005.
Marc et al., "K004 Orally active aminopeptidase a inhibitors reduce blood pressure by blocking the brain renin-angiotensin system activity: a new strategy for the treatment of hypertension", *Archives of Cardiovascular Disease*, 102: S114, 2009.
Miura et al., "Increase in antinociceptive effect of [Leu$^5$] Enkephal in after intrathecal administration of mixture of three peptidase inhibitors", *The Tokai Journal of Experimental and Clinical Medicine*, 38(2): 62-70, 2013.
Office Action issued in European Patent Application No. 14150608.9, dated May 13, 2014.
Takai et al., "Therapeutic applications of chymase inhibitors in cardiovascular diseases and fibrosis", *Journal of Pharmacology*, 501(1-3): 1-8, 2004.
Yahiro et al., "Beneficial Effects of a Combination Therapy with ACE and Chymase Inhibitors in Hamster Heart Failure Model", *Journal of Cardial Failure*, 11(9): S271, 2005.
Yahiro et al., "Chymase Inhibitors", *Current Pharmaceutical Design*, 19: 3065-3071, 2013.
Yang et al., "Structural Insights into Central Hypertension Regulation by Human Aminopeptidase A", *Journal of Biological Chemistry*, 288(35): 25638-25645, 2013.

*Primary Examiner* — Raymond J Henley, III
(74) *Attorney, Agent, or Firm* — Norton Rose Fulbright US LLP (57) ABSTRACT

The present invention relates to a pharmaceutical composition comprising a. at least one aspartyl aminopeptidase inhibitor and at least one angiotensin-converting-enzyme (ACE) inhibitor, or b. at least one aspartyl aminopeptidase inhibitor and at least one chymase inhibitor. In an embodiment, the pharmaceutical composition comprises at least one aspartyl aminopeptidase inhibitor and at least one angiotensin-converting-enzyme (ACE) inhibitor and at least one chymase inhibitor. Furthermore, the invention relates to a pharmaceutical composition possessing inhibitory activity against a. aspartyl aminopeptidase and angiotensin-converting-enzyme (ACE), or b. against aspartyl aminopeptidase and chymase. In a third aspect, the invention relates to a kit of parts comprising a. a pharmaceutical composition comprising an aspartyl aminopeptidase inhibitor and a pharmaceutical composition comprising an angiotensin-converting-enzyme (ACE) inhibitor, or b. a pharmaceutical composition comprising an aspartyl aminopeptidase inhibitor and a pharmaceutical composition comprising a chymase inhibitor, or c. a pharmaceutical composition comprising an aspartyl aminopeptidase inhibitor and a pharmaceutical composition comprising an angiotensin-converting-enzyme (ACE) inhibitor and a pharmaceutical composition comprising a chymase inhibitor. The invention also relates to a method for decreasing the blood pressure in a subject by administering a therapeutically effective amount of a pharmaceutical composition according to the invention to the subject. In another aspect, the invention relates to a method for treating a disease related to the RAS in a subject by administering a therapeutically effective amount of a pharmaceutical composition according to the invention to the subject.

23 Claims, 5 Drawing Sheets

COMPOSITIONS AND METHODS FOR THE TREATMENT OF DISEASES RELATED TO THE RENIN-ANGIOTENSIN-SYSTEM

CROSS-REFERENCE TO RELATED APPLICATIONS

This application is a national phase application under 35 U.S.C. §371 of International Application No. PCT/EP2014/077452 filed 11 Dec. 2014, which claims priority to European Patent Application No. 13196740.8 filed 11 Dec. 2013 and European Patent Application No. 14150608.9 filed 9 Jan. 2014. The entire contents of each of the above-referenced disclosures is specifically incorporated by reference herein without disclaimer.

FIELD OF THE INVENTION

The present invention relates to pharmaceutical compositions, kits and methods for the treatment of diseases related to the renin-angiotensin system (RAS), such as e.g. hypertension. The pharmaceutical compositions according to the invention comprise at least one aspartyl aminopeptidase inhibitor and at least one angiotensin-converting-enzyme (ACE) inhibitor, or at least one aspartyl aminopeptidase inhibitor and at least one chymase inhibitor.

BACKGROUND TO THE INVENTION

Hypertension is a pathological increase in blood pressure that is expected to affect around 50% of the human population until 2025 (Ref.: WHO, A Global Brief on Hypertension, World Health Day 2013). Elevated blood pressure (above 135 mmHg systolic) is known to be the major cause of cardiovascular diseases including stroke, heart failure, chronic kidney disease, atherosclerosis and many others. Multiple drugs interfering with different biological regulatory systems have been developed to treat hypertension, among which the ACE inhibitors take over a major role. ACE inhibitors (ACEI) are currently used in the treatment of hypertension, heart failure, different types of nephropathies, and type II diabetes.

Their potency in lowering blood pressure is based on their mechanism of blocking the formation of Angiotensin II (Ang II, Ang 1-8, Ang-(1-8)), which is a peptide hormone of the renin-angiotensin-system (RAS), an important regulatory system for blood pressure and fluid balance.

The RAS, as a peptide hormone system being a crucial therapeutic target in the treatment of cardiovascular diseases, regulates multiple physiologic functions including fluid homeostasis and salt balance. The effector molecules of the RAS, the angiotensin peptides, exert their physiologic effects via specific receptor molecules expressed in a variety of cell types and tissues. Furthermore the RAS is also reported to take over important regulatory roles in the immune system and in cell proliferation, converting the system to a promising target for therapeutic interferences for the treatment of above mentioned pathologic conditions, with a huge potential in the field of immune regulation and neoplastic diseases.

Angiotensin peptides and their metabolites are produced via the concerted action of different angiotensin processing enzymes that are proteases, cleaving off one or more amino-acids either from the C-terminus of precursor molecules (Mono-, Di-, Tricarboxypeptidases), the N-terminus (Mono-, Di, Triaminopeptidases) or cleaving the peptide at an internal position of the molecule (Endopeptidases).

Enzymes that have been reported to be involved in angiotensin metabolism include renin, angiotensin-converting-enzyme (ACE), angiotensin-converting-enzyme 2 (ACE2), neutral endopeptidase (NEP), aminopeptidase A (APA), aminopeptidase N (APN), carboxypeptidase a (CPA), thimet oligopeptidase (THOP) or chymase. Further molecular features adding complexity to this important regulatory system include an overlapping substrate specificity of angiotensin processing enzymes involved (e.g.: ACE2 has both, Angiotensin I and Angiotensin II as a substrate) as well as the presence of enzymes carrying out similar reactions (e.g. ACE and chymase both convert Ang I to Ang II). The important role of products and substrates of the enzymatic reactions mediated by some of these enzymes favors them as targets for drugs aimed to interfere with angiotensin mediated physiologic functions.

Aminopeptidases have been shown to be involved in the metabolism and regulation of peptide hormones including angiotensins, bradykinins, vasopressins, endothelins, apelins, dynorphins and many other vasoactive peptides and neuropeptides.

Aminopeptidases have further been described to affect cell growth and cell division leading to therapeutic applications in the field of neoplastic diseases like solid tumors or leukemia. The most prominent aminopeptidase inhibitor in clinical use is Bestatin (Trading name: Ubenimex), which is used in the treatment of solid tumors (Ota et al., Biotherapy 1992). More recently, it has been shown that the inhibition of aminopeptidase A (APA) might be a strategy for treating hypertension, which is based on the mechanism of preventing the formation of Angiotensin III in the brain, which is thought to be a cause of central hypertension (Wright et al., International Journal of Hypertension 2012).

Yang et al. (J Biol Chem 2013, 288 (35): 25638-25645) relates to human aminopeptidase A (APA) crystal structures.

Fournie-Zaluski et al. (PNAS USA 2004, 101 (20): 7775-7780) describes the brain renin-angiotensin system and selective APA inhibitors EC33 and RB150.

Masaaki et al. (Tokai J Exp Clin Med 2013, 38 (2): 62-70) describes antinociceptive effects of [Leu$^5$]enkephalin.

Marc et al. (Archives of Cardiovascular Disease 2009, 102: S114) describes selective APA inhibitors EC33 and RB150.

Eiji Yahiro et al. (Current Pharmaceutical Design, 2013, 19: 3065-3071) describes chymase inhibitors.

Eiji Yahiro et al. (J Cardial Failure, 2005, 11 (9): S271) relates to effects of chymase inhibitors in a hamster heart failure model.

Takai et al. (Eur J Pharmacology, 2004: 1-8) relates to chymase inhibitors in cardiovascular disease and fibrosis.

Chaikuad et al. (BMC Structural Biology 2012, 12 (1): 14) provides a structure of human aspartyl aminopeptidase complexed with a substrate analogue.

Leckie et al. (Curr Med Chem, 2005, 3 (1): 23-32) reviews RAS targeting.

Kitamura et al. (Am J of Physiology, 1999, 276 (5): H1664-H1671) relates to aminiopeptidase P inhibition.

A major challenge for the strategy of preventing the formation of Angiotensin III in the brain by blocking APA is represented by an effective, safe and non-invasive drug delivery. Blockade of APA in the brain leads to favored pharmacologic changes in the central RAS as the formation of the pro-hypertensive peptide Angiotensin III from Angiotensin II is blocked. In contrast to the brain, where Angiotensin III is reported to cause hypertension, Angiotensin II is taking over pro-hypertensive activity in the periphery (tissues and plasma). Therefore, in case that APA is also responsible for formation of Ang 2-8 from Ang 1-8 in the periphery, a complete block of APA in the periphery could lead to unwanted side effects caused by excessive peripheral Ang 1-8 accumulation. Many of the data generated to support the efficacy of the recently developed APA blocker for treating hypertension has been obtained following intra-cerebroventricular (i.c.v.) injection, which is very unlikely to be implemented as a standard anti-hypertensive treatment in humans. Although an inactive pro-drug (RB150) for the APA inhibitor has been developed to overcome this problem, the presence of the active metabolite (EC-33) in the periphery cannot be excluded, as RB150 is known to be a oxidation dependent dimer of EC-33 and many reductive systems are present in human plasma and tissue (e.g. Glutathione-System) that might be capable of reducing the oxidized inactive dimer RB150 to the active metabolite EC-33.

Thus, there is a need for safe and effective treatment of hypertension to avoid cardiovascular complications. The present invention provides pharmaceutical compositions and methods for effectively decreasing blood pressure and for treating diseases related to the RAS.

BRIEF DESCRIPTION OF THE INVENTION

In one aspect, the present invention relates to a pharmaceutical composition comprising
  a. at least one aspartyl aminopeptidase inhibitor and at least one angiotensin-converting-enzyme (ACE) inhibitor, or
  b. at least one aspartyl aminopeptidase inhibitor and at least one chymase inhibitor.

In an embodiment, the pharmaceutical composition comprises at least one aspartyl aminopeptidase inhibitor and at least one angiotensin-converting-enzyme (ACE) inhibitor and at least one chymase inhibitor.

In a further aspect, the invention relates to a pharmaceutical composition possessing inhibitory activity against
  a. aspartyl aminopeptidase and angiotensin-converting-enzyme (ACE), or
  b. against aspartyl aminopeptidase and chymase.

In a third aspect, the invention relates to a kit of parts comprising
  a. a pharmaceutical composition comprising an aspartyl aminopeptidase inhibitor and a pharmaceutical composition comprising an angiotensin-converting-enzyme (ACE) inhibitor, or
  b. a pharmaceutical composition comprising an aspartyl aminopeptidase inhibitor and a pharmaceutical composition comprising a chymase inhibitor, or
  c. a pharmaceutical composition comprising an aspartyl aminopeptidase inhibitor and a pharmaceutical composition comprising an angiotensin-converting-enzyme (ACE) inhibitor and a pharmaceutical composition comprising a chymase inhibitor.

In a fourth aspect, the invention relates to a method for decreasing the blood pressure in a subject by administering a therapeutically effective amount of a pharmaceutical composition according to the invention to the subject.

In a fifth aspect, the invention relates to a method for treating a disease related to the RAS in a subject by administering a therapeutically effective amount of a pharmaceutical composition according to the invention to the subject.

BRIEF DESCRIPTION OF THE FIGURES

FIG. 3: In vitro and ex vivo sensitivity of human aminopeptidase A (APA) for Amastatin. The formation of Ang 2-8 from Ang 1-8 was investigated in an in vitro system further described in Example 2 (left panel). APA activity is represented by the formation rate of Ang 2-8 given in pg Ang 2-8/ml per minute. For ex vivo analysis of the sensitivity of human APA for inhibition by Amastatin, plasma samples were pretreated as indicated followed by quantification of resulting Ang 1-8 levels by LC-MS/MS (right panel).

FIG. 5: Pharmacologic effects of the sequential intravenous administration of Lisinopril and Amastatin to an SHR rat. Equilibrium Ang 1-8 (left panel) and Ang 1-7 (right panel) levels in the SHR rat were measured by LC-MS/MS. Concentrations of the peptides are given in pg/ml plasma. LC-MS/MS signals with a signal-to-noise ratio below 10 were considered to be below the lower limit of quantification and are marked as "<" in the graph.

DETAILED DESCRIPTION OF THE INVENTION

In one aspect, the present invention relates to a pharmaceutical composition comprising
  a. at least one aspartyl aminopeptidase inhibitor and at least one angiotensin-converting-enzyme (ACE) inhibitor, or
  b. at least one aspartyl aminopeptidase inhibitor and at least one chymase inhibitor.

In an embodiment, the pharmaceutical composition comprises at least one aspartyl aminopeptidase inhibitor and at least one angiotensin-converting-enzyme (ACE) inhibitor. In an embodiment, the pharmaceutical composition comprises at least one aspartyl aminopeptidase inhibitor and at least one angiotensin-converting-enzyme (ACE) inhibitor and at least one chymase inhibitor.

In a further aspect, the invention relates to a pharmaceutical composition possessing inhibitory activity against
  a. aspartyl aminopeptidase and angiotensin-converting-enzyme (ACE), or
  b. against aspartyl aminopeptidase and chymase.

In a third aspect, the invention relates to a kit of parts comprising
  a. a pharmaceutical composition comprising an aspartyl aminopeptidase inhibitor and a pharmaceutical composition comprising an angiotensin-converting-enzyme (ACE) inhibitor, or b. a pharmaceutical composition comprising an aspartyl aminopeptidase inhibitor and a pharmaceutical composition comprising a chymase inhibitor, or c. a pharmaceutical composition comprising an aspartyl aminopeptidase inhibitor and a pharmaceutical composition comprising an angiotensin-converting-enzyme (ACE) inhibitor and a pharmaceutical composition comprising a chymase inhibitor.

In one embodiment, the pharmaceutical composition possesses inhibitory activity against aspartyl aminopeptidase and angiotensin-converting-enzyme (ACE). In one embodiment, the pharmaceutical composition possesses inhibitory activity against aspartyl aminopeptidase and angiotensin-converting-enzyme (ACE) and chymase.

Whenever it is referred to an activity herein, e.g. an enzymatic activity or an inhibitory activity or the like, it is clear to a skilled person that such activity is (or is not) particularly exerted under physiologic conditions, e.g. under conditions similar to the conditions in the human or animal body, such as e.g. a physiologically acceptable pH and/or temperature, physiological concentrations of the enzyme(s) and/or substrate(s), and/or with physiologically acceptable buffers and/or excipients etc. The same applies to affinities as mentioned herein, e.g. the affinity of an enzyme to one or more substrates etc.

Aminopeptidases are enzymes that cleave off amino acids from the N-terminus of proteins and/or peptides. Aminopeptidases might cleave one, two, three or more amino acid residues off the N-terminus of a protein and/or peptide (mono- di-, tri- or oligoaminopeptidases respectively). Aminopeptidases are further classified via their preferred substrates. For example, glutamyl aminopeptidases have a preference to cleave substrates with glutamic acid on their N-terminus, whereas methionine aminopeptidases have a preference for substrates with the amino acid methionine at the N-terminus.

Accordingly, the term "aspartyl aminopeptidase" as used herein refers to an aminopeptidase that is able to cleave off at least the N-terminal aspartic acid (D, Asp) of a peptide or protein. However, the aspartyl aminopeptidase may also cleave off one or more further amino acids following the N-terminal Asp. For example, a di-amino peptidase cleaving off the two N-terminal amino acids from Ang 1-8 (Sequence: DRVYIHPF, SEQ ID NO: 1) is also an aspartyl aminopeptidase according to the definition above. In an embodiment, the aspartyl aminopeptidase can cleave off one or more N-terminal amino acids of Ang 1-5, Ang 1-6, Ang 1-7, Ang 1-8, Ang 1-9, and/or Ang 1-10, i.e. has Ang 1-5, Ang 1-6, Ang 1-7, Ang 1-8, Ang 1-9, and/or Ang 1-10 as substrate(s). In an embodiment, the aspartyl aminopeptidase can cleave off one or more N-terminal amino acids of Ang 1-7 (also referred to as Ang-(1-7)) and/or Ang 1-8 and/or Ang 1-10 (also referred to as Ang 1). In an embodiment, the aspartyl aminopeptidase has a certain affinity to one or more substrates having an Asp at its N-terminus. In an embodiment, said affinity to one or more substrates having an Asp at its N-terminus is higher than its affinity to substrates not having Asp at their N-terminus (e.g. an amino acid other than Asp) under the same or similar conditions (e.g. same or similar physiologic conditions). In an alternative embodiment, said affinity to one or more peptide substrates having an Asp at its N-terminus is higher than its affinity to peptide substrates having an identical or similar amino acid sequence except for the N-terminal Asp, i.e. not having Asp at their N-terminus (e.g. having an amino acid other than Asp at their N-terminus) under the same or similar conditions. Accordingly, in said embodiment the aspartyl aminopeptidase is selective for one or more substrates with an N-terminal Asp, i.e. one or more substrates with an N-terminal Asp are the preferred substrate(s) for the aspartyl aminopeptidase according to the invention. In one embodiment, the aspartyl aminopeptidase is DNPEP (also known as DAP or ASPEP, EC 3.4.11.21). For further reference to aspartyl aminopeptidase, especially human aspartyl aminopeptidase, and also other aminopeptidases, see e.g. Chaikuad et al. 2012, BMC Structural Biology.

In one embodiment, the aspartyl aminopeptidase is not APA. In one embodiment, the aspartyl aminopeptidase is not APN. In one embodiment, the aspartyl aminopeptidase is neither APA nor APN.

Figure 2:
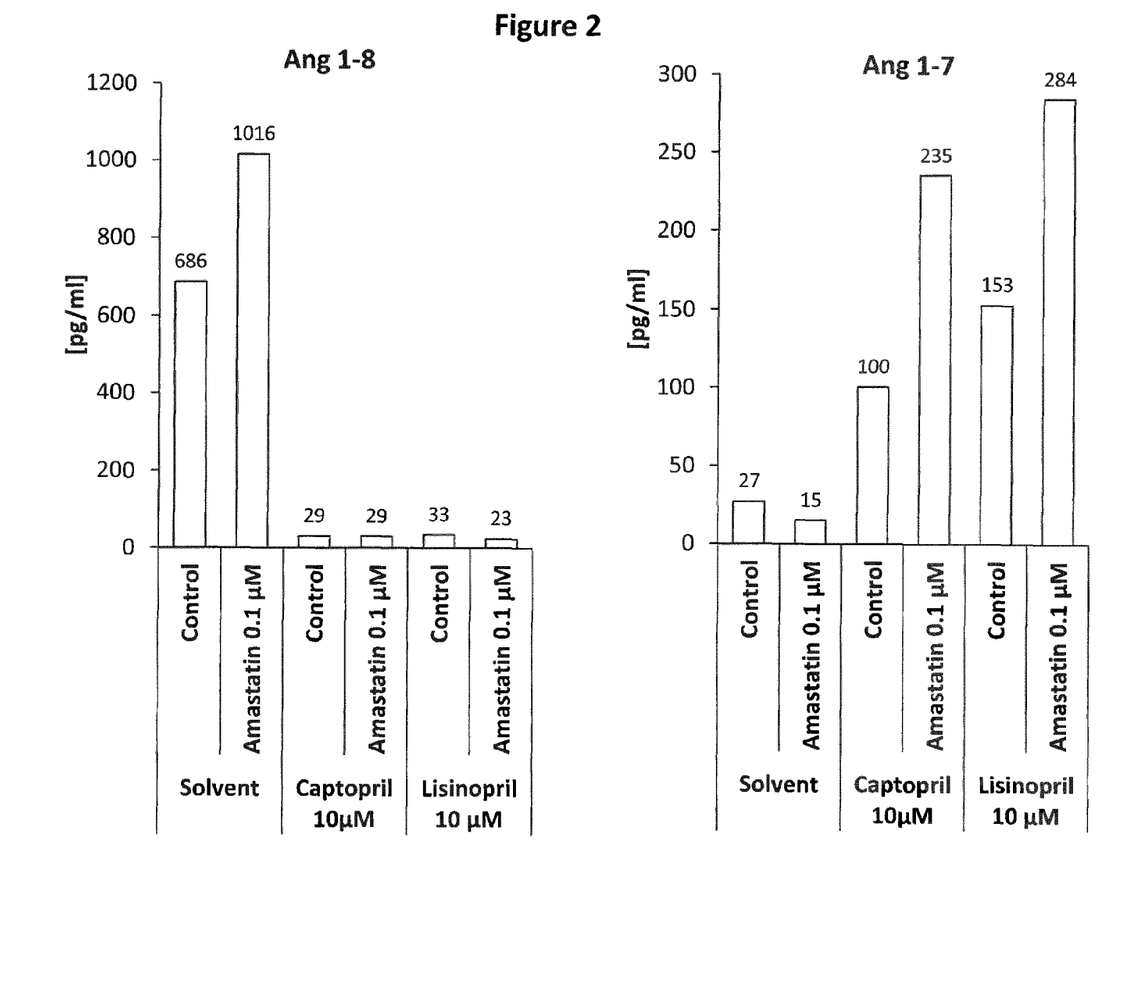
FIG. 2: Pharmacologic effects of the combination of Amastatin and Lisinopril or Captopril on Ang 1-8 levels and Ang 1-7 levels in human whole blood ex vivo. Samples were pretreated with inhibitors as indicated and Angiotensin concentrations were measures by LC-MS/MS. Values are given in pg/ml of the indicated peptides.
Figure 3:
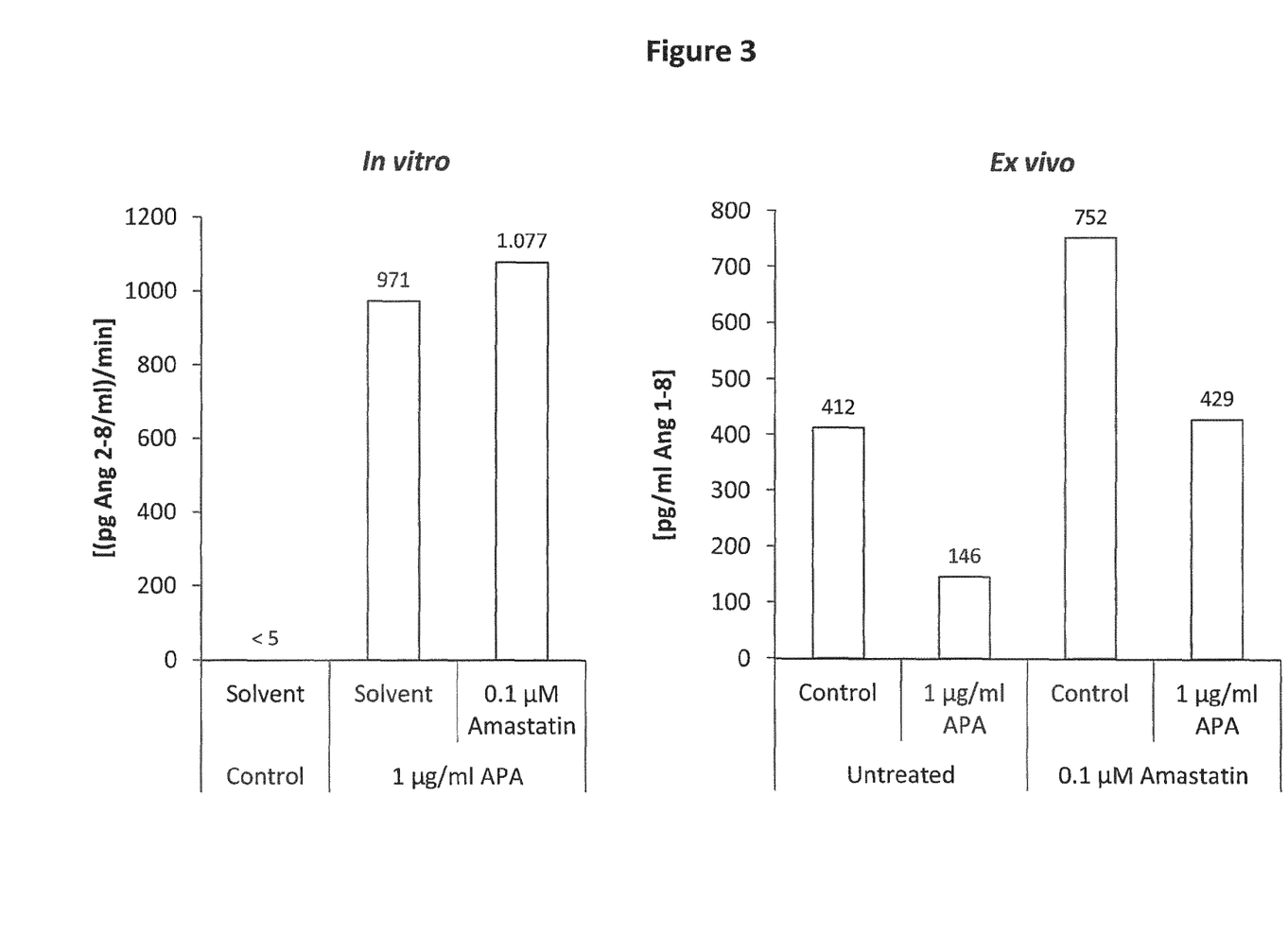
Figure 4:
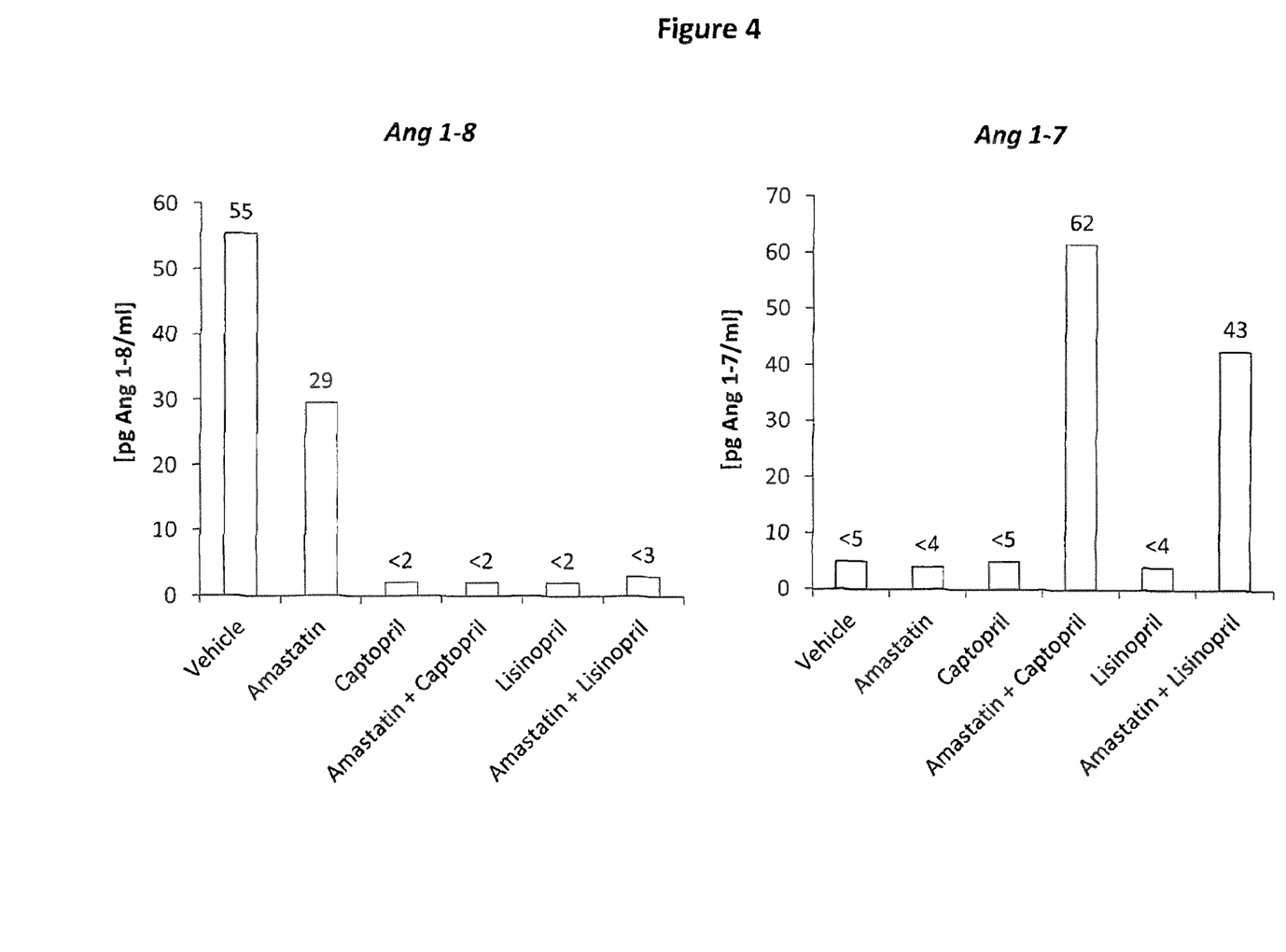
FIG. 4: Pharmacologic effects of the combined administration of Amastatin and Lisinopril or Captopril on Ang 1-8 and Ang 1-7 levels in Balb/C mice. Ang 1-8 (left panel) and Ang 1-7 (right panel) levels in Balb/c mice were measured by LC-MS/MS following 4 h treatment with indicated drugs. Concentrations of the peptides are given in pg/ml plasma. LC-MS/MS signals with a signal-to-noise ratio below 10 were considered to be below the lower limit of quantification and are marked as "<" in the graph.

However, individual enzymes might have more than one peptidase activity leading to broad substrate specificities among aminopeptidases. For example, aminopeptidase A (APA, EC 3.4.11.7) is a monoaminopeptidase encoded by the ENPEP gene and is reported to have glutamyl and aspartyl aminopeptidase activity, meaning that it can cleave either glutamic acid or aspartic acid residues from the N-terminus of polypeptides. In an embodiment, the aspartyl aminopeptidase has aspartyl aminopeptidase activity and one or more other aminopeptidase activities. APA's aspartyl aminopeptidase activity was also investigated in our studies on Ang 2-8 formation by APA (FIG. 3), as the N-terminus of Ang 1-8, the substrate for APA mediated Ang 2-8 formation, is aspartic acid (Ang 1-8 sequence: DRVYIHPF, SEQ ID NO: 1). Interestingly, despite a reported inhibitory activity for Amastatin against APA, Amastatin did not block the Ang 1-8 converting aspartyl aminopeptidase activity of APA (FIG. 3) at Amastatin concentrations that were shown to substantially change angiotensin metabolism in human plasma in the absence and presence of Lisinopril (FIG. 2). Therefore we conclude that Amastatin blocks Ang 1-8 degradation via an APA independent mechanism that plays a major role in angiotensin metabolism in the periphery. As the N-terminal sequence of Ang 1-7 and Ang 1-8 are identical and thus, both are substrates for an aspartyl aminopeptidase, it could be assumed that this APA independent degradation of Ang 1-7 and Ang 1-8 is blocked by Amastatin. Actually, we have shown that Amastatin inhibits an aspartyl aminopeptidase other than APA that is involved in the metabolism of angiotensins, e.g. the degradation of Ang 1-7 and/or Ang 1-8, and thus, is relevant to the RAS. In an embodiment, the aspartyl aminopeptidase inhibitor inhibits at least one aspartyl aminopeptidase involved in the degradation of Ang 1-7 and/or Ang 1-8. In an embodiment, the aspartyl aminopeptidase inhibitor inhibits at least one aspartyl aminopeptidase other than APA that is involved in the degradation of Ang 1-7 and/or Ang 1-8. Surprisingly, an increase in Ang 1-7 levels is observed (FIG. 2 and FIG. 4, right panels), while Ang 1-8 levels are unaffected by Amastatin in the presence of ACE inhibitors. The huge difference regarding Ang 1-7 levels between ACE inhibitor treated human whole blood and blood treated with the combination of Amastatin and an ACE inhibitor clearly shows a strong synergy of the molecular mechanisms underlying the combined treatment. Similar synergic effects were observed following in vivo administration of the inventive compositions to mice (FIG. 4).

This novel and unique pharmacologic effect on angiotensin levels induced by the combined action of an aspartyl aminopeptidase inhibitor and an ACE inhibitor might also explain the surprising efficacy of the combination of Amastatin and the ACE inhibitor Lisinopril in the treatment of hypertension in SHR rats and provides for new combinations of drugs in new treatments of hypertension. Preferably the treated subject is a human.

In one embodiment, the aspartyl aminopeptidase is involved in the RAS or in the metabolism of angiotensin(s). For example, the aspartyl aminopeptidase is involved in the peripheral RAS (i.e. the RAS in the periphery), e.g. the systemic RAS and/or the RAS in one or more tissues (except brain and/or spinal cord).

The term "aspartyl aminopeptidase inhibitor" as used herein refers to any pharmaceutically active ingredient or compound inhibiting the activity of at least one aspartyl aminopeptidase (i.e. possessing inhibitory activity against at least one aspartyl aminopeptidases), or to a pro-drug thereof. Accordingly, the aspartyl aminopeptidase inhibitor may also be a pro-drug that is activated upon or after administration to the subject.

The term "pro-drug" as used herein refers to a partially or completely inactive drug that is initially administered to the body in an inactive (or less than fully active) form, and then becomes converted to its active form either through the normal metabolic processes of the body, or through one or more activators that are administered to the subject.

For example, the pharmaceutical composition according to the invention may comprise Amastatin and Lisinopril linked via a labile covalent bond and thereby inactivated, which is cleaved in the body of the subject (e.g. by enzymes or substances inherent to the body of the subject or administered to the subject), and thus releases the two active enzyme inhibitors.

In an embodiment, the aspartyl aminopeptidase inhibitor inhibits the activity of at least one aspartyl aminopeptidase involved in the RAS or angiotensin metabolism. In one embodiment, the aspartyl aminopeptidase inhibitor selectively inhibits DNPEP (also known as DAP, EC 3.4.11.21), i.e. the aspartyl aminopeptidase inhibitor is a selective DNPEP inhibitor. Whether or not a compound inhibits or selectively inhibits the activity of at least one aspartyl aminopeptidase involved in the RAS or angiotensin metabolism can be tested by in vitro or ex vivo methods known in the art, e.g. as described in the Examples, or as described in WO 2013/182237.

In another embodiment, the aspartyl aminopeptidase inhibitor inhibits Ang 1-8 degradation via an APA independent mechanism (e.g. if administered in an in vitro or ex vivo system without ACE inhibitors and/or chymase inhibitors). This can also be tested as known in the art, or described in the Examples or in WO 2013/182237.

In an embodiment, the aspartyl aminopeptidase inhibitor increases the systemic Ang 1-8 level when given without ACE inhibitors and/or chymase inhibitors, but does not increase (or not substantially increase), or decrease (or substantially decrease) the systemic Ang 1-8 level when given in combination with at least one ACE inhibitor and/or at least one chymase inhibitor. In an embodiment the aspartyl aminopeptidase inhibitor increases the systemic Ang 1-7 level to a certain extent (e.g. 1, 2, 3, 4, 5, 10, 15, or 20%) when given without ACE inhibitors and/or chymase inhibitors. In an embodiment the aspartyl aminopeptidase inhibitor increases the systemic Ang 1-7 level to a certain extent when given without ACE inhibitors and/or chymase inhibitors, and substantially increases (or synergistically increases) the systemic Ang 1-7 level when given in combination with at least one ACE inhibitor and/or at least one chymase inhibitor. In an embodiment the aspartyl aminopeptidase inhibitor increases (or substantially increases) the systemic Ang 1-7 level when given in combination with at least one ACE inhibitor and/or at least one chymase inhibitor, but does not increase (or not substantially increase) the systemic Ang 1-7 level when given without ACE inhibitors and/or chymase inhibitors. In an embodiment, the aspartyl aminopeptidase inhibitor is administered systemically and increases the systemic Ang 1-8 level when given without ACE inhibitors and/or chymase inhibitors, but does not increase (or not substantially increase), or decrease (or substantially decrease) the systemic Ang 1-8 level when given systemically in combination with at least one ACE inhibitor and/or at least one chymase inhibitor. In an embodiment the aspartyl aminopeptidase inhibitor is administered systemically and increases (or substantially increases) the systemic Ang 1-7 level when given systemically in combination with at least one ACE inhibitor and/or at least one chymase inhibitor, but does not increase (or not substantially increase) the systemic Ang 1-7 level when given without ACE inhibitors and/or chymase inhibitors.

The term "increase" as used herein with regard to angiotensin levels (e.g. Ang II and/or Ang 1-7 levels) refer to the increase of the respective level caused by the given effector, e.g. the given compound, substance, drug, or pharmaceutical composition. In one embodiment, the level is increased at least 10, 20, 30, 40, 50, 60, 70, 80, or 90%, or any range in between these %-values, compared to the respective level under the same or similar conditions in a sample without the effector, e.g. the level in plasma measured prior to administration of the effector. In an embodiment, the effector is an enzyme inhibitor or a combination of enzyme inhibitors, e.g. one or more ACE inhibitors, chymase inhibitors, and/or aspartyl aminopeptidase inhibitors. The person skilled in the art can easily determine whether a compound, substance, drug, or pharmaceutical composition increases the respective level, either by methods described in the present invention (especially in the examples), or by methods known in the prior art. The methods for determination of an increase in a respective level may be in vitro and/or in vivo methods.

Accordingly, the term "decrease" as used herein with regard to angiotensin levels (e.g. Ang II and/or Ang 1-7 levels) refer to the decrease of the respective level caused by the given effector, e.g. the given compound, substance, drug, or pharmaceutical composition. In one embodiment, the level is decreased at least 10, 20, 30, 40, 50, 60, 70, 80, or 90%, or any range in between these %-values, compared to the respective level under the same or similar conditions in a sample without the effector, e.g. the level in plasma measured prior to administration of the effector. In an embodiment, the effector is an enzyme inhibitor or a combination of enzyme inhibitors, e.g. one or more ACE inhibitors, chymase inhibitors, and/or aspartyl aminopeptidase inhibitors. The person skilled in the art can easily determine whether a compound, substance, drug, or pharmaceutical composition decreases the respective level, either by methods described in the present invention (especially in the examples), or by methods known in the prior art. The methods for determination of a decrease in a respective level may be in vitro and/or in vivo methods.

The term "substantially" as used herein means an effect (e.g. in increase or decrease of a level) of at least 10, 20, 30, 40, 50, 60, 70, 80, 90, or 100%, or any range in between these %-values.

In an embodiment the aspartyl aminopeptidase inhibitor increases (or substantially increases) the systemic Ang 1-7 level when given in combination with at least one ACE inhibitor and/or at least one chymase inhibitor, but does not increase (or not substantially increase) the systemic Ang 1-7 level by more than 10, 20, 30, 40, or 50%, or any range in between these %-values, when given without ACE inhibitors and/or chymase inhibitors, both compared to an untreated control, in particular when administered systemically.

In an embodiment, the aspartyl aminopeptidase inhibitor is not a methionine aminopeptidase inhibitor. For example, the aspartyl aminopeptidase inhibitor does not possess inhibitory activity against methionine aminopeptidases (e.g. does not inhibit methionine aminopeptidase EC 3.4.11.18), or its affinity to substrates having a methionine (Met, M) at their N-terminus is lower than its affinity to substrates having an amino acid other than methionine at their N-terminus (e.g. Asp) under the same or similar conditions.

In an embodiment, the aspartyl aminopeptidase inhibitor is not a selective aminopeptidase A inhibitor. In an embodiment, the aspartyl aminopeptidase inhibitor is not a selective aminopeptidase N inhibitor. In a further embodiment, the aspartyl aminopeptidase is not a selective aminopeptidase A inhibitor and not a selective aminopeptidase N inhibitor.

The term "selective" as used herein refers to an inhibitor selectively inhibiting said specific enzyme. In an embodiment, the affinity and/or inhibitory constant of a selective aminopeptidase inhibitor (e.g. a selective aminopeptidase X inhibitor) for its target aminopeptidase (e.g. aminopeptidase X) is higher than the affinity and/or inhibitory constant for at least one other aminopeptidase (i.e. an aminopeptidase other than its target aminopeptidase, e.g. aminopeptidase Y). For example, the affinity and/or inhibitory constant of a selective aminopeptidase A inhibitor for aminopeptidase A is higher than the affinity and/or inhibitory constant for at least one other enzyme, e.g. aminopeptidase N (APN, EC 3.4.11.2). In an embodiment, the affinity and/or inhibitory constant of a selective aminopeptidase inhibitor is at least 5, 10, 20, 30, 40, 50, 60, 70, 80, 90, or 100-fold higher, or any range in between these values, for its preferred target compared to other targets, i.e. the affinity and/or inhibitory constant is multiplied by a factor of 5, 10, 20, 30, 40, 50, 60, 70, 80, 90, or 100, or more, or any range in between. In one embodiment, the affinity and/or inhibitory constant of the aspartyl aminopeptidase inhibitor for its selective (or preferred) target (e.g. any aspartyl aminopeptidase other than APA) is at least 1, 2, 3, 4, 5, 10, 20, 30, 40, 50, 60, 70, 80, 90, or 100-fold higher than the affinity and/or inhibitory constant of the same inhibitor for APA, or any range in between these values. In one embodiment, the affinity and/or inhibitory constant of the aspartyl aminopeptidase inhibitor for its selective (or preferred) target aspartyl aminopeptidase is at least 1, 2, 3, 4, 5, 10, 20, 30, 40, 50, 60, 70, 80, 90, or 100-fold higher than the affinity and/or inhibitory constant of the same inhibitor for APN, or any range in between these values. In one embodiment, the affinity and/or inhibitory constant of the aspartyl aminopeptidase inhibitor for APA is less than 100-fold higher than the affinity and/or inhibitory constant of the aspartyl aminopeptidase inhibitor for APN.

Amastatin is reported to be an inhibitor of APA (EC 3.4.11.7). However, its affinity to APA is low compared to its affinity to other known aminopeptidases, such as e.g. APN (EC 3.4.11.2), and potentially unknown aminopeptidases. Amastatin was shown to be 40-fold more potent in inhibiting APN (IC50=0.2 µM) compared to APA (IC50=8 µM). (Ahmad and Ward 1990, JPET). Thus, according to the above definition. Amastatin is not a selective APA inhibitor. According to the state of the art. Amastatin could rather be regarded as glutamyl aminopeptidase inhibitor. However, as disclosed herein. Amastatin inhibits an aspartyl aminopeptidase other than APA that is involved in the RAS. Thus, Amastatin is an aspartyl aminopeptidase according to the definition herein.

In an embodiment, the aspartyl aminopeptidase inhibitor is not RB150 and/or EC-33. In an embodiment, the aspartyl aminopeptidase inhibitor is not Bestatin. In an embodiment, the aspartyl aminopeptidase inhibitor is not a compound as disclosed in U.S. Pat. No. 6,340,708. In one embodiment, the aspartyl aminopeptidase inhibitor does not cross the blood-brain barrier (or does not substantially cross the blood-brain barrier). In one embodiment, the aspartyl aminopeptidase inhibitor is a pro-drug and said pro-drug does not cross the blood-brain barrier (or does not substantially cross the blood-brain barrier).

In an embodiment, the aspartyl aminopeptidase inhibitor is administered systemically and does not cross the blood-brain barrier (or does not substantially cross the blood-brain barrier). In an embodiment, the aspartyl aminopeptidase inhibitor is administered systemically and its concentration (w/v) in the periphery (e.g. in a blood sample, a blood derived sample, and/or in a peripheral tissue sample) is at least 2-, 3-, 4-, 5-, 6-, 7-, 8-, 9-, 10-, or 100-fold or more (or any range in between) higher than its concentration (w/v) in the brain and/or spinal cord. In an embodiment, the aspartyl aminopeptidase inhibitor is administered systemically and its effect on the peripheral RAS is at least 2-, 3-, 4-, 5-, 6-, 7-, 8-, 9-, 10-, or 100-fold or more (or any range in between) higher than its effect on the central RAS. The effect on the peripheral RAS can be determined by determining the Ang 1-7 concentration in a blood or serum sample. The effect on the central RAS can be determined by determining the Ang 1-7 concentration in a cerebrospinal fluid sample or in a homogenized tissue sample. An increase is determined in relation to a sample of the untreated sample or untreated sample donor.

In one embodiment, the aspartyl aminopeptidase inhibitor is a small molecule. In an alternative embodiment, the aspartyl aminopeptidase inhibitor is a protein or peptide, e.g. an antibody. In one embodiment, the aspartyl aminopeptidase inhibitor is an inhibitory nucleic acid, such as a siRNa, shRNA, miRNA, or a vector encoding such nucleic acids.

In one embodiment, the aspartyl aminopeptidase inhibitor is Amastatin or a derivative thereof.

Accordingly, the aspartyl aminopepeptidase inhibitor used in the pharmaceutical composition of the invention might be Amastatin or a chemical derivative thereof. Amastatin was shown herein to inhibit an aspartyl aminopeptidase that is crucially involved in the metabolism of Ang 1-8 and Ang 1-7. It was further shown herein that the observed effects on Ang 1-8 and Ang 1-7 metabolism were independent of APA (FIG. 3). Amastatin is known to be a drug with more than one target among aminopeptidases (e.g. APA and APN). Therefore, suitable derivatives of Amastatin could show an improved selectivity and/or affinity for the aspartyl aminopeptidase being responsible for the effects on angiotensin metabolism observed (FIG. 2). Moreover, the bioavailability could be improved by derivatives, which would facilitate the use of Amastatin in the pharmaceutical compositions, kits and methods according to the invention, especially for the treatment of hypertension or cancer in humans.

In another embodiment, the aspartyl aminopeptidase inhibitor is not Amastatin.

In an embodiment, the activity of at least one aspartyl aminopeptidase (e.g. DNPEP) is inhibited at least 10, 20, 30, 40, 50, 60, 70, 80, or 90%, or any range in between these %-values.

The term "ACE inhibitor" as used herein refers to any pharmaceutically active ingredient or compound inhibiting the activity of Angiotensin-Converting-Enzyme (ACE, EC 3.4.15.1) or any ACE like activity leading to a reduced formation of Ang 1-8 from Ang 1-10, or a pro-drug thereof. ACE is an enzyme involved in the RAS, in particular in the degradation and formation of angiotensins. Similar to chymase. ACE is a carboxypeptidase and converts Ang I to Ang 1-8. ACE is a metalloprotease that is built up by an N-terminal and a C-terminal domain. The two domains possess different substrate specificities and their slightly different molecular structure can also result in differences in the affinity of ACE inhibitors for the two individual domains. Moreover, different isoforms of ACE are known to be expressed in humans, including membrane attached, soluble, full length and truncated forms. In an embodiment. ACE inhibitors include inhibitors of ACE and ACE isoforms. ACE is broadly expressed throughout multiple tissues and fluids of the human body (Maluf-Meiken et al., International Journal of Hypertension 2012; Hattori et al., Hypertension 2000, Deddish et al., Hypertension 1998).

Accordingly, in an embodiment, the ACE inhibitor inhibits the conversion of Ang I to Ang 1-8. In an embodiment, the conversion of Ang I to Ang 1-8 is inhibited by the ACE inhibitor by at least 10, 20, 30, 40, 50, 60, 70, 80, or 90%, or any range in between these %-values.

In one embodiment, the ACE inhibitor is a small molecule. In an alternative embodiment, the ACE inhibitor is a protein or peptide, e.g. an antibody, or an inhibitory nucleic acid, such as a siRNa, shRNA, miRNA, or a vector encoding such nucleic acids.

The ACE inhibitor may be selected from the group consisting of alacepril, benazepril, benazeprilat, captopril, ceronapril, cilazapril, delapril, enalapril, enalaprilat, fosinopril, imidapril, lisinopril, moexipril, moveltopril, perindopril, quinapril, quinaprilat, ramipril, ramiprilat, spirapril, temocapril, trandolapril, zofenopril, and pharmaceutically acceptable salts thereof. In one embodiment, the ACE inhibitor is selected from agents that have been marketed already, e.g. benazepril, benazaprilat, ramipril and ramiprilat, quinapril, quinaprilat, lisinopril, trandolapril, enalapril, or enalaprilat.

In an embodiment, the ACE inhibitor is Lisinopril and/or Captopril.

It is well known that ACE is one of the key players in Ang 1-8 formation from Ang 1-10. However, there are other enzymes known to be involved in Ang 1-8 formation from Ang 1-10. Chymase (EC 3.4.21.39), a carboxypeptidase, is reported to be the major enzyme responsible for Ang 1-8 formation in the heart and in blood vessels (Dell'Italia et al., Curr. Opin. Cardiol. 2002) and, like ACE, carries out the enzymatic cleavage of Ang 1-10 to yield Ang 1-8. In recent years, chymase inhibitors have been suggested to support the action of ACE inhibitors in the treatment of heart failure by achieving a more efficient block of Ang 1-8 formation in the heart (Matsumoto et al., Circulation 2003).

The observed beneficial effect on blood pressure by combining an aspartyl aminopeptidase inhibitor with an ACE inhibitor is based on a synergistic mechanism between both inhibitors, which is known to involve the block of formation of Ang 1-8 by ACE-mediated cleavage of Ang 1-10. Knowing that chymase and ACE take over identical molecular roles in the formation of Ang 1-8, it can be expected that the combination of an aspartyl aminopeptidase inhibitor with a chymase inhibitor, or a combination of an aspartyl aminopeptidase inhibitor with a chymase inhibitor and an ACE inhibitor, shows similar or even better efficacy in the treatment of RAS associated diseases including hypertension. However, the field of application for the aspartyl aminopeptidase-chymase inhibitor combination might differ from the aspartyl aminopeptidase-ACE inhibitor combination as it is known that the relative contribution of ACE and chymase to Ang 1-8 formation differs significantly between various tissues. The person skilled in the art can easily select the preferred combination for the specific indication or for the specific effect he wants to achieve with the pharmaceutical composition or methods according to the invention.

Thus, in one embodiment, the aspartyl aminopeptidase inhibitory activity is combined with a chymase inhibitory activity, either instead of the ACE inhibitory activity or in addition thereto.

In an embodiment, the chymase inhibitor is selected from Chymostatin, NK3201, SUN-C8257, TY51184, BCEAB, Y-40018, and derivates and combinations thereof (see e.g. Doggrell, Sheila A, Exp. Opinion on Therapeutic Patents 2008).

The terms "inhibitor" or "inhibitory activity" as used herein refer to the inhibition of the activity of respective enzyme, e.g. ACE and/or aspartyl aminopeptidase and/or chymase. In one embodiment, the enzyme is inhibited at least 10, 20, 30, 40, 50, 60, 70, 80, or 90%, or any range in between these %-values, compared to the activity of the respective enzyme under the same or similar conditions in a sample without inhibitor or inhibitory activity, e.g. the enzyme activity in plasma measured prior to administration of the inhibitor. The person skilled in the art can easily determine whether a compound, substance, drug, or pharmaceutical composition inhibits the respective enzyme, either by methods described in the present invention (especially in the examples), or by methods known in the prior art. The methods for determination of inhibitory activity may be in vitro, ex vivo and/or in vivo methods. Thus, the terms aspartyl aminopeptidase inhibitor, ACE inhibitor, chymase inhibitor, and/or any other enzyme inhibitor referred to herein are compounds that inhibit the respective enzyme and are terms that are well established in the art (see e.g. the references cited herein).

Accordingly, in one embodiment, the pharmaceutical composition comprises at least one aspartyl aminopeptidase inhibitor and at least one chymase inhibitor, and optionally at least one ACE inhibitor. In another embodiment, the pharmaceutical composition comprises at least one aspartyl aminopeptidase inhibitor and at least one ACE inhibitor, and optionally at least one chymase inhibitor. In yet another embodiment, the pharmaceutical composition comprises at least one aspartyl aminopeptidase inhibitor and at least one chymase inhibitor and at least one ACE inhibitor. In still another embodiment, the pharmaceutical composition comprises at least one aspartyl aminopeptidase inhibitor and at least one ACE inhibitor, but does not comprise a chymase inhibitor.

In one embodiment of the present invention,
a. the at least one aspartyl aminopeptidase inhibitor and the at least one ACE inhibitor, or
b. the at least one aspartyl aminopeptidase inhibitor and the at least one chymase inhibitor, or
c. the at least one aspartyl aminopeptidase inhibitor and the at least one ACE inhibitor and the at least one chymase inhibitor are combined in one single molecule.

Said single molecule may be any single molecule having the activity of the at least one aspartyl aminopeptidase inhibitor and the at least one ACE inhibitor, or the at least one aspartyl aminopeptidase inhibitor and the at least one chymase inhibitor, or the at least one aspartyl aminopeptidase inhibitor and the at least one ACE inhibitor and the at least one chymase inhibitor. Said single molecules do not necessarily show structural similarity to any separate aspartyl aminopeptidase inhibitor, chymase inhibitor or ACE inhibitor, provided that these molecules possess the corresponding inhibitory activities for aspartyl aminopeptidase and ACE and/or chymase. Accordingly, the single molecule may be a molecular fusion of inhibitors structurally similar to one or more of said separate inhibitors, or it may be a totally different molecule having the respective combined inhibitory activities.

Accordingly, the pharmaceutical composition according to the invention may comprise one single molecule possessing inhibitory activity against
  a. aspartyl aminopeptidase and angiotensin-converting-enzyme (ACE), or
  b. against aspartyl aminopeptidase and chymase.

Optionally, said single molecule may comprise additional activities.

In one embodiment, at least one aspartyl aminopeptidase inhibitor, the at least one ACE inhibitor and/or the at least one chymase inhibitor are combined in a single molecule, i.e. a single molecule exerts an aspartyl aminopeptidase inhibitory activity as well as an ACE inhibitory activity and/or a chymase activity.

For example, dual inhibitors for endothelin-converting-enzyme (ECE) and neutral endopeptidase (NEP), or ACE and NEP, have already been tested for efficacy in several disease models (Mellin et al. 2005, J cardiovasc Pharmacol. and Jandeleit-Dahm et al. 2006, Journal of Human Hypertension). Accordingly, the pharmaceutical composition or the kit of the present invention may comprise a single molecule having aspartyl aminopeptidase inhibitory activity as well as ACE inhibitory activity and/or chymase inhibitory activity, and optionally further activities. In other embodiments, separate compounds are used as aspartyl aminopeptidase inhibitor, ACE inhibitory and/or chymase inhibitor. Preferably, the aspartyl aminopeptidase inhibitor, ACE inhibitory and/or chymase inhibitor has a higher inhibitory activity on the respective named enzyme than for the other of these enzymes. In further embodiments, the inhibitors used according to any embodiment of the invention may be chemically linked, e.g. by a linker moiety or directly via a chemical bond. For example (and as described above), the pharmaceutical composition according to the invention may comprise Amastatin and Lisinopril linked via a labile covalent bond and thereby inactivated, which is cleaved in the body of the subject (e.g. by enzymes or substances inherent to the body of the subject or administered to the subject), and thus releases the two active enzyme inhibitors. In said case, the pharmaceutical composition is one single molecule and is also a pro-drug.

A person skilled in the art can easily determine whether or not a single molecule has the appropriate inhibitory activities as described herein, e.g. by methods as described herein. Accordingly, the skilled person can easily screen compounds, single molecules or pharmaceutical compositions for such activities. Furthermore, a skilled person can make such single molecules with the required activities, e.g. by introducing a linker as described above, or as known in the art.

Optionally, the pharmaceutical composition may comprise further active ingredients. In one embodiment, the pharmaceutical composition does not comprise further active ingredients. In one embodiment, the pharmaceutical composition does not comprise a neutral endopeptidase (NEP) inhibitor (e.g. SCH39370, Chappell et al.; Nephrol Dial Transplant. 2001; 16 Suppl 1:22-6.).

The present invention also relates to a kit as further described above. Said kit of parts may comprise one or more of the respective pharmaceutical compositions with the given activities as described herein. For example, the kit comprises at least two components, e.g. at least one aspartyl aminopeptidase inhibitor and at least one ACE inhibitor or at least one chymase inhibitor. The kit may further comprise a manual, e.g. describing how to combine and/or administer the components of the kits. One or more components of the kit (or all components of the kit) may be combined prior to administration and administered as a mixture. Also, one or more components of the kit (or each component of the kit) may be administered separately, either simultaneously or sequentially, either by the same or by different routes of administration.

The subject may be a human or animal. In one embodiment, the subject is a mammal such as a mouse, rat or primate (e.g. a marmoset or monkey). The subject can be a non-human animal. The method or composition also has a veterinary use. The subject to be treated may be a farm animal for example, a cow or bull, sheep, pig, ox, goat or horse or may be a domestic animal such as a dog or cat. The animal may be any age, or a mature adult animal. In an embodiment, the subject is a human.

In one embodiment, the pharmaceutical composition, kit or method as defined herein is for the treatment of a disease related to the Renin-Angiotensin system (RAS). Such a disease may be related to a dysfunction of the RAS or a dysregulation of the RAS.

It is well known in the art that the RAS is dysregulated in cardiovascular and other diseases, such as hyperplastic and/or neoplastic diseases, inflammation and autoimmune diseases. In particular, the Ang-II levels are increased and/or the Ang-(1-7) levels are decreased in said conditions; or it is described that an increase in the Ang-(1-7) level (e.g. by administration of Ang-(1-7)), and/or a decrease in the Ang-II level is advantageous in said conditions. The present invention shows the synergistic effect of the combination of the two claimed classes of compounds on Ang-II and/or Ang-(1-7), and thus, provides the rationale for treating said conditions or diseases with the pharmaceutical compositions as described herein.

The disease related to the RAS may be a hyperplastic and/or neoplastic disease and/or a cardiovascular disease and/or immune system related disease. For example, the cardiovascular disease is hypertension and/or heart failure. The disease related to the RAS (and its dysfunction) may be selected from the group consisting of hypertension, left ventricular dysfunction, hypertrophic cardiomyopathy, diabetic cardiac myopathy, supraventricular and ventricular arrhythmias, atrial fibrillation, atrial flutter, detrimental vascular remodeling, myocardial infarction and its sequelae, antheroscleorosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomecular sclerosis, proteinuria of primary renal disease, and also renal vascular hypertension, diabetic retinophathy; other vascular disorders, such as migraine, peripheral vascular disease. Raynaud's disease, luminal hyperplasia, endothelial dysfunction, cognitive dysfunction (such as Alzheimer's disease), glaucoma, stroke, neoplastic diseases, inflammation and conditions related thereto, and autoimmune diseases.

The neoplastic disease may be cancer, especially a cancer that is related to increased Ang II levels and/or a cancer in that an increase in Ang-(1-7) is advantageous. The cancer may be selected from the group consisting of lung cancer, prostate cancer, breast cancer, especially triple negative breast cancer, osteosarcoma, pediatric sarcomas, and brain cancer. For further reference to the relation of a dysregulated RAS and several diseases, see for example, Gallagher et al.; Curr Med Chem. 2014; 21 (21):2417-23; Passos-Silva et al.; Clin Sci (Lond). 2013 April; 124 (7):443-56. doi: 10.1042/CS20120461; Simões e Silva et al.; Br J Pharmacol. 2013; June; 169 (3):477-92. doi: 10.1111/bph.12159; Gallagher et al.; Curr Cancer Drug Targets. 2011 May; 11 (4):394-404; Cook et al.; Cancer Res. 2010 Nov. 1; 70 (21):8319-28. doi: 10.1158/0008-5472.CAN-10-1136; Ender et al.; Mol Med Rep. 2014 August; 10 (2):804-10. doi: 10.3892/mmr.2014.2266; Gallagher, et al.; Proceedings of the AACR Special Conference on Tumor Invasion and Metastasis; Jan. 20-23, 2013; San Diego, Calif. Philadelphia (Pa.): AACR; Cancer Res 2013; 73 (3 Suppl):Abstract C66; Gallagher, P. E. and E. A. Tallant (2004); Carcinogenesis 25 (11): 2045-2052).

References herein to "hypertension", also known as "high blood pressure", refer to when the blood pressure within the arteries of a patient is abnormally high. Prolonged high blood pressure can put an increased strain on the heart as it pumps blood to circulate around the body, and as a result many cardiovascular diseases are associated with high blood pressure. Normal blood pressure has a diastolic blood pressure of less than 85 mmHg. High normal blood pressure has a diastolic blood pressure between 85 and 89 mmHg. Mild hypertension corresponds to a diastolic blood pressure between 90-104 mmHg. Moderate hypertension has to a diastolic blood pressure between 105 and 114 mmHg. Severe hypertension has a diastolic blood pressure higher than 115 mmHg. Abnormal blood pressure is also determined from the systolic blood pressure (when the diastolic pressure is less than 90 mmHg). Normal blood pressure has a systolic blood pressure of less than 140 mmHg. Borderline systolic hypertension shows a systolic blood pressure between 140 and 159 mmHg. Isolated systolic hypertension has a systolic blood pressure higher than 160 mmHg (see, Cecil: Essentials of Medicine, Third Edition by Andreoli et al. W. B. Saunders Company (1993)). Hypertension is diagnosed in an adult over 18 years old if the average of two or more blood pressure measurements on at least two visits is 90 mmHg or higher diastolic or 140 mmHg systolic. Children and pregnant women have a lower blood pressure, so a blood pressure over 120/80 (i.e., 120 mmHg systolic blood pressure/80 mmHg diastolic blood pressure) indicates hypertension.

The invention further relates to the use of at least one ACE inhibitor and/or chymase inhibitor, and at least one aspartyl aminopeptidase inhibitor for the manufacture of a medicament for the treatment of a disease related to the RAS.

In an embodiment, the pharmaceutical composition is administered systemically (or is for use in systemic administration, or is formulated for systemic administration), e.g. is administered orally (or is for use in oral administration). For example, the pharmaceutical composition is formulated as a tablet or capsule, or as a solution for infusion or injection. In an embodiment, the pharmaceutical composition is not administered into the brain (or not for use in intra-cerebral administration, i.e. not for use in administration into the brain). In an embodiment, the pharmaceutical composition is not administered intracerebroventricularly (i.c.v. or ICV) or is not for intracerebral delivery.

The pharmaceutical compositions according to the present invention may further comprise one or more pharmaceutically acceptable excipients, diluents or carriers. The carrier, diluent and/or excipient must be "acceptable" in the sense of being compatible with the other ingredients of the composition and not deleterious to the recipient thereof. Typically such compositions comprise a "pharmaceutically acceptable carrier" or "excipient" as known and called for by acceptable pharmaceutical practice, see e.g. Remingtons Pharmaceutical Sciences, 16th edition (1980) Mack Publishing Co. Examples of such carriers include sterilised carriers such as saline. Ringers solution or dextrose solution, optionally buffered with suitable buffers to a pH within a range of 5 to 8.

The active principle of the pharmaceutical compositions, kits and methods according to the invention is the inhibition (especially peripheral or systemic inhibition) of at least one aspartyl aminopeptidase in combination with the inhibition of Ang 1-8 formation (e.g. by ACE or chymase blockade). The effect of said active principle is an increase in the Ang-(1-7) level and/or a decrease in the Ang-II level. Accordingly, in one embodiment, the level of Ang-(1-7) is increased by the administration of the pharmaceutical composition. In a further embodiment, the level of Ang-II is decreased by the administration of the pharmaceutical composition. In a further embodiment, the level of Ang-(1-7) is increased and the level of Ang-II are decreased by the administration of the pharmaceutical composition.

In one embodiment, the pharmaceutical composition according to the invention comprises one or more pro-drugs of the respective inhibitors instead of the inhibitor(s) itself (i.e. instead of the active enzyme inhibitor(s)), as described above.

It is highly advantageous to increase the level of Ang-(1-7) within the blood system because Ang-(1-7), for example, has been shown to have vasoprotective and anti-proliferative effects (see Ocaranza M P, Jalil J E (2012), Raizada M K, Ferreira A J, Ocaranza M P et al. (2010), and Shenoy V et al.). Decreasing the Ang-(1-8) level has also shown beneficial effects in protecting the heart, vessels and kidney from adverse cardiovascular remodelling (for example anti-hypertrophic and anti-fibrotic effects) in hypertension as well as heart failure (Fyhrquist et al. 1995. Journal of Human Hypertension). Thus, without being bound by theory, increasing Ang-(1-7) and/or decreasing Ang-(1-8) levels in circulation has advantageous effects on the cardiovascular system of the body and can be used in the treatment, including prophylactic treatment, of diseases related to the RAS, especially cardiovascular diseases.

The term "level" as used herein refers to the amount of the substance (e.g. Ang-(1-7), and/or Ang 1-8) in a sample obtained from a subject, e.g. in a blood sample or in a blood derived sample, such as e.g. a plasma or serum sample. The level may be given as amount of the substance per volume of the sample, e.g. as pg/ml.

In a fourth aspect, the invention relates to a method for decreasing the blood pressure in a subject by administering a therapeutically effective amount of a pharmaceutical composition according to the invention to the subject.

In a fifth aspect, the invention relates to a method for treating a disease related to the RAS in a subject by administering a therapeutically effective amount of a pharmaceutical composition according to the invention to the subject.

In an embodiment, the pharmacologic effect of the pharmaceutical compositions, the kits and the methods according to the invention is mediated by affecting the RAS (e.g. the peripheral or systemic RAS). Accordingly, in an embodiment, the pharmaceutical compositions or the kits or the methods of the invention affect the RAS, e.g. the peripheral or systemic RAS.

The terms "periphery" or "peripheral" as used herein refer to any parts of the body except the brain (including the spinal cord), e.g. the circulatory system and/or one or more tissues. Accordingly, the terms "periphery" or "peripheral" as used herein refer to any parts of the body except those that are separated by the blood-brain-barrier.

The term "systemic" as used herein refers to a route of administration into the circulatory system, and/or refers to a site of pharmacologic action or localization of a pharmaceutical composition in the circulatory system, and/or refers to an effect via the circulatory system or an effect on the circulatory system (e.g. on blood pressure). In an embodiment, the site of pharmacologic action is independent of the route of administration. In an embodiment, the pharmaceutical composition is administered into the peripheral circulatory system, and/or its site of pharmacologic action is in the peripheral circulatory system, and/or it is distributed in the peripheral circulatory system, and/or exerts its pharmacologic effect via the peripheral circulatory system, and/or has an effect on the peripheral circulatory system. In an embodiment, the pharmaceutical composition is not administered intracerebroventricularly (i.c.v. or ICV) and/or not by intracerebral delivery. Systemic administration can take place e.g. via enteral administration (absorption of the drug through the gastrointestinal tract) or parenteral administration (generally injection, infusion, or implantation). A systemically administered pharmaceutical composition may be distributed within the circulatory system but exert its effect in a specific tissue or body area. For example, chymase is not present in blood plasma, but is present inter alia in cardiac tissue. Accordingly, a chymase inhibitor may be administered systemically and its effect can be measured e.g. in cardiac tissue. With regard to a systemic effect, the pharmaceutical composition is administered systemically and its effect is present or can be measured in the circulatory system and/or in at least one tissue or body area different from the brain and/or spinal cord. In contrast, a local effect is restricted to any local area of the body, to which the drug is administered. A systemic effect can e.g. be measured by analysing a blood sample (or a blood derived sample, such as e.g. plasma or serum) or a tissue sample (e.g. a peripheral tissue sample) of the subject.

Methods for the preparation or manufacture of pharmaceutical compositions according to the invention are well known to those skilled in the art. The pharmaceutical compositions or the kits according to the invention may further comprise instructions for use.

Effective doses and treatment regimes for administering the composition are generally determined empirically and may be dependent on factors such as the age, weight and health status of the patient and disease or disorder to be treated. Such factors are within the area of the person skilled in the art. The dosage of the ACE inhibitor or the chymase inhibitor or the aspartyl aminopeptidase inhibitor to be administered to a subject is generally between 1 µg/kg to 150 mg/kg, between 0.1 mg/kg and 100 mg/kg, between 0.5 mg/kg and 50 mg/kg, between 1 and 25 mg/kg or between 1 and 10 mg/kg of the subject's body weight and might be administered one, two, three or more times a day. For example, the dose may be 1 mg/kg, 10 mg/kg, 30 mg/kg, 60 mg/kg, 100 mg/kg.

If a range is given herein, any such range shall include any range in between the given ranges (i.e. any range in between and including the lower and the upper limit of the range). If a list of values is given herein, any such list of values shall include any whole number or fraction values in between the given example values (e.g. any such values in between the listed example values).

The administration of a dose may be systemically, e.g. orally or by infusion or injection.

The administration of a dose may be repeated one or more times as necessary, for example, three times daily, once every day, once every 2 days, once a week, once every two weeks, once a month, once every 3 months, once every 6 months, or once every 12 months. When the composition is used in a further combination with other therapeutically active agents, the individual components may be administered either together or separately, simultaneously, sequentially, concurrently or consecutively, in separate or combined pharmaceutical formulations, by any convenient route. If administered separately or sequentially, the combination and the therapeutically active agent(s) can be administered in any order.

When combined in the same formulation it will be appreciated that the components must be stable and compatible with each other and the other components of the formulation and may be formulated for administration. When formulated separately they may be provided in any convenient formulation, for example in such a manner as known for the ACE inhibitor or chymase inhibitor or aspartyl aminopeptidase inhibitor agents in the art. When used in combination with a second therapeutic agent active against the same disease, the dose of each component may differ from that when the composition is used alone. Appropriate doses will be readily appreciated by those skilled in the art.

Treatment can be therapeutic, prophylactic or preventative. The subject will be one who is in need thereof. Those in need of treatment may include subjects already suffering from a particular medical disease in addition to those who may develop the disease in the future. Thus, the composition described herein can be used for prophylactic or preventative treatment. In this case, the composition described herein is administered to the subject in order to prevent or delay the onset of one or more aspects or symptoms of the disease. The subject can be asymptomatic. The subject may have a genetic predisposition to the disease. A prophylactically effective amount of the composition is administered to such subject. A prophylactically effective amount is an amount, which prevents or delays the onset of one or more aspects or symptoms of a disease described herein.

The composition described herein may also be used in methods of therapy. The term "therapy" encompasses alleviation, reduction, or prevention of at least one aspect or symptom of a disease. For example, the composition described herein may be used to ameliorate or reduce one or more aspects or symptoms of a disease described herein.

The composition described herein is used in an effective amount for therapeutic, prophylactic or preventative treatment. A therapeutically effective amount of the composition described herein is an amount effective to ameliorate or reduce one or more aspects or symptoms of the disease. The composition described herein may also be used to treat, prevent, or cure the disease described herein.

The composition described herein need not affect a complete cure, or eradicate every symptom or manifestation of the disease to constitute a viable therapeutic treatment. As is recognised in the pertinent field, drugs employed as therapeutic agents may reduce the severity of a given disease state, but need not abolish every manifestation of the disease to be regarded as useful therapeutic agents. Similarly, a prophylactically administered treatment does not need to be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

The term "therapeutically effective amount" refers to an amount (dose) of a substance, e.g. an amount of therapeutic composition that is sufficient to prevent, inhibit, halt, or allow an improvement in the disease being treated.

EXAMPLES

Example 1

Figure 1:
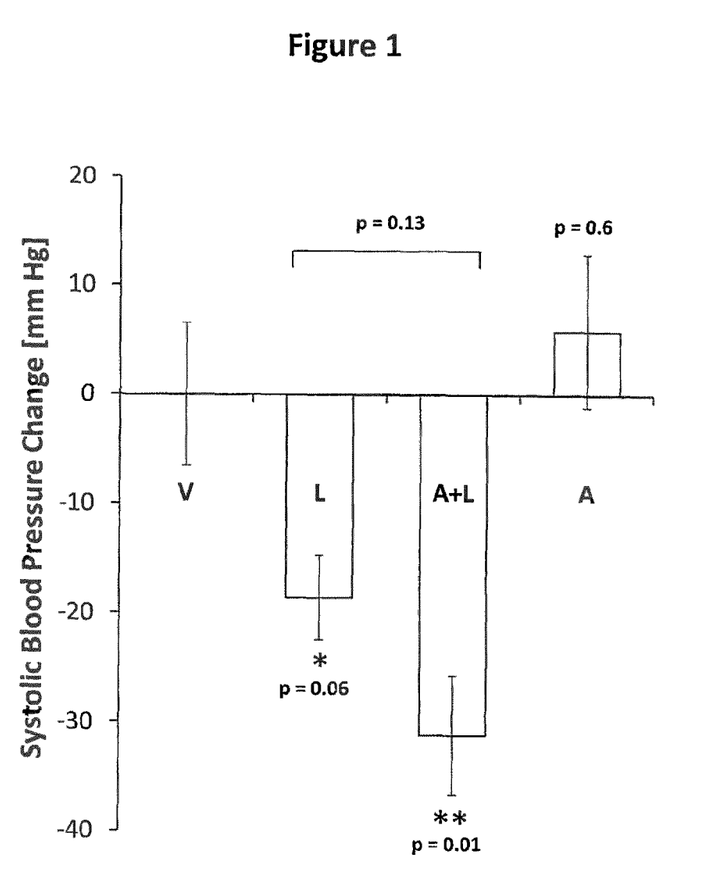
FIG. 1: Blood pressure lowering effect for Lisinopril (L), Amastatin (A) and the combination of Amastatin and Lisinopril (A+L) in SHR rats is shown in mmHg difference compared to vehicle treated (V) animals. 5 animals were treated per group and mean values are given+/−SEM. Statistical analysis was performed using Student's T-Test.

Effects of the combined administration of Amastatin and Lisinopril on blood pressure in male SHR rats (FIG. 1).
Methods Twenty male 16-week-old SHR rats were used for investigation of short-term effects of the new drug combination on systolic blood pressure. Prior to starting the treatment procedure, rats were conditioned to the experimental procedure by daily blood pressure measurements using the tail-cuff method for 1 week. Rats were randomized to 4 different treatment groups consisting of 5 animals that were treated either with vehicle (PBS), 40 mg/kg Lisinopril in PBS, 40 mg/kg Amastatin in PBS or a combination of 40 mg/kg Lisinopril and 40 mg/kg Amastatin in PBS by intra-peritoneal injection of the compounds each morning for a treatment period of 7 days. Daily blood pressure measurements were performed 4 h following drug administration and continued throughout the whole treatment period. Blood-pressure data were evaluated by calculating the relative change in systolic blood pressure compared to the vehicle group at day 7 of drug administration. Statistical comparison between the groups was conducted by using Student's T-test.
Results Mean body weight and baseline systolic blood pressure of SHR rats were determined at the beginning of the treatment period resulting in a mean body weight of 283 g and mean systolic blood pressure of 196 mmHg. Following 7 days of daily oral administration of different compounds and compound combinations, systolic blood pressure was monitored by tail-cuff method and the relative changes compared to vehicle treated control rats (V) mean values are shown with corresponding standard errors of the mean (+/−SEM) (FIG. 1).
Treatment of SHR rats with Lisinopril (L) resulted in a significant decrease in systolic blood pressure of 18.6+/−3.9 mmHg compared to vehicle treated animals (p=0.06). Treatment with Amastatin (A) alone resulted in a moderate but not significant increase in mean systolic blood pressure (5.8+/−7.0 mmHg) compared to vehicle treated animals (p=0.60). The combined administration of Amastatin and Lisinopril (A+L) resulted in a highly significant decrease in blood pressure of 31.2+/−5.5 mmHg compared to vehicle treated animals (p=0.01), strongly exceeding the blood pressure lowering effect of Lisinopril alone (18.6+/−3.9 mmHg).

Example 2

Pharmacologic effects of Amastatin and Lisinopril or Captopril on Ang 1-8 and Ang 1-7 levels in human whole blood (FIG. 2).
Methods Blood was collected from a human healthy volunteer using a standard heparin blood collection tube. Recombinant human renin was added to whole blood at a concentration of 100 pg/ml in order to simulate RAS hyper-activation. Drugs and combinations were added to different plasma samples at indicated final concentrations and combinations (FIG. 2) using appropriate solvent controls for each compound or combination tested. Following an incubation period of 60 min at 37° C., samples were stabilized by addition of protease inhibitors and Ang 1-8 and Ang 1-7 levels were measured by mass spectrometry.
Results Ang 1-8 and Ang 1-7 levels were measured following 1 h of incubating the compounds with human heparinized whole blood (plus recombinant human renin) at 37° C. (FIG. 2). The aspartyl aminopeptidase inhibitor Amastatin resulted in a strong increase of Ang 1-8 compared to vehicle control in the absence of ACE inhibitors (686 pg/ml vs. 1016 pg/ml), while Ang 1-7 levels were reduced (27 pg/ml vs. 15 pg/ml). ACE inhibition alone, either by 10 μM Captopril or 10 μM Lisinopril, resulted in a profound decrease in Ang 1-8 levels to 29 pg/ml and 33 pg/ml respectively while Ang 1-7 levels were strongly increased by the ACE inhibitors to 100 pg/ml and 153 pg/ml respectively. Surprisingly, despite the effect that Amastatin alone strongly increases Ang 1-8 levels, Ang 1-8 remained low when both, ACE inhibitors and Amastatin were present in the same sample (Amastatin+Captopril: 29 pg/ml, Amastatin+Lisinopril: 23 pg/ml).
Despite the finding that Amastatin alone showed a decrease in Ang 1-7 in human whole blood, the combination of the ACE inhibitors with Amastatin resulted in a strong synergistic increase in Ang 1-7 levels (1.8-2.4 fold) when comparing with samples treated with the ACE inhibitors alone (Captopril: 235 pg/ml vs. 100 pg/ml, Lisinopril: 284 pg/ml vs. 153 pg/ml).

Example 3

In vitro and ex vivo sensitivity of human APA for Amastatin (FIG. 3).
Methods:

The conversion of Ang 1-8 to Ang 2-8 by APA has been analyzed in an in vitro system (left panel) using 100 ng/ml Ang 1-8 incubated at 37° C. for 10 min in the presence or absence of 1 μg/ml APA (recombinant human ENPEP, R&D; Cat. no. 2499-ZN) and/or 0.1 μM Amastatin. APA activity was determined by measuring Ang 2-8 formation using LC-MS/MS. The Ang 2-8 formation rate is given in pg Ang 2-8/ml per minute. For investigation of APA activity and the impact of Amastatin on endogenous angiotensin metabolism ex vivo (right panel), heparin blood was collected from healthy volunteers. Following isolation of plasma by centrifugation at 2500 g for 10 min, 100 pg/ml recombinant human renin (Sigma, R2779) was added to heparin plasma, followed by a 60 min incubation at 37° C. in the presence or absence of 1 μg/ml APA and/or 0.1 μM Amastatin as indicated. Following the incubation period, samples were cooled on ice, stabilized by the addition of protease inhibitors and analyzed for Ang 1-8 levels by LC-MS/MS.
Results:

APA activity assays have been performed to evaluate the impact of Amastatin on APA activity in vitro (FIG. 3, left panel). As expected, 1 μg/ml APA efficiently converts Ang 1-8 to Ang 2-8 resulting in an Ang 1-8 formation rate of 971 pg Ang 2-8/ml per minute. Surprisingly, 0.1 μM Amastatin did not affect APA activity in vitro giving an Ang 2-8 formation rate of 1077 pg Ang 2-8/ml per minute. APA activity in human plasma was assessed by the measurement of Ang 1-8 levels in human heparin plasma following addition of recombinant human renin and 60 min of ex vivo incubation at 37° C. (right panel). The addition of 1 μg/ml APA to the plasma sample resulted in a significant reduction of Ang 1-8 levels compared to the untreated control sample (146 pg/ml vs. 412 pg/ml). Incubation in the presence of 0.1 µM Amastatin resulted in a remarkable increase of Ang 1-8 levels in plasma as observed in previous experiments (412 pg/ml vs. 752 pg/ml). Surprisingly, the presence of 0.1 µM Amastatin did not affect the activity of human APA in plasma as indicated by the comparable or even stronger reduction of Ang 1-8 levels by 1 µg/ml APA in the presence of 0.1 µM Amastatin (323 pg/ml vs. 266 pg/ml without Amastatin).

Example 4

Pharmacologic effects of the combined administration of Amastatin and Lisinopril or Captopril on Ang 1-8 and Ang 1-7 levels in Balb/C mice (FIG. 4).
Methods
Female, 6-week-old Balb/c mice were treated with vehicle (PBS), 50 mg/kg Lisinopril in PBS, 40 mg/kg Captopril in PBS, 40 mg/kg Amastatin in PBS, a combination of 40 mg/kg Lisinopril in and 40 mg/kg Amastatin in PBS or a combination 40 mg/kg Captopril and 40 mg/kg Amastatin in PBS by intra-peritoneal injection. Mice were sacrificed 4 h following drug administration and blood was collected in the presence of protease inhibitors suitable for stabilization of angiotensin peptides in the collected sample. Following centrifugation of blood at 2500 g for 5 min at 4° C., Ang 1-8 and Ang 1-7 was quantified in the plasma samples by LC-MS/MS analysis.
Results
Baseline circulating Ang 1-8 and Ang 1-7 levels in Balb/c mice were 55 pg/ml and below 5 pg/ml (LLOQ) respectively. Amastatin treatment resulted in a decrease in circulating Ang 1-8 at 4 h following drug administration, while the Ang 1-7 level remained unaffected and keeping below the lower quantification limit of 4 pg/ml. Treatment of mice with the ACE inhibitors Lisinopril and Captopril resulted in a significant decrease of plasma Ang 1-8 levels down below the lower quantification limit of 2-3 pg/ml plasma. An increase of Ang 1-7 following ACE inhibitor treatment was not observed following administration of ACE inhibitors alone. The combined administration of Amastatin in combination with either Captopril or Lisinopril resulted in a surprising increase of Ang 1-7 levels in murine plasma (62 pg/ml and 43 pg/ml respectively), while Ang 1-8 levels remained suppressed below the lower quantification limit of 2-3 pg/ml plasma.

Example 5

Figure 5:
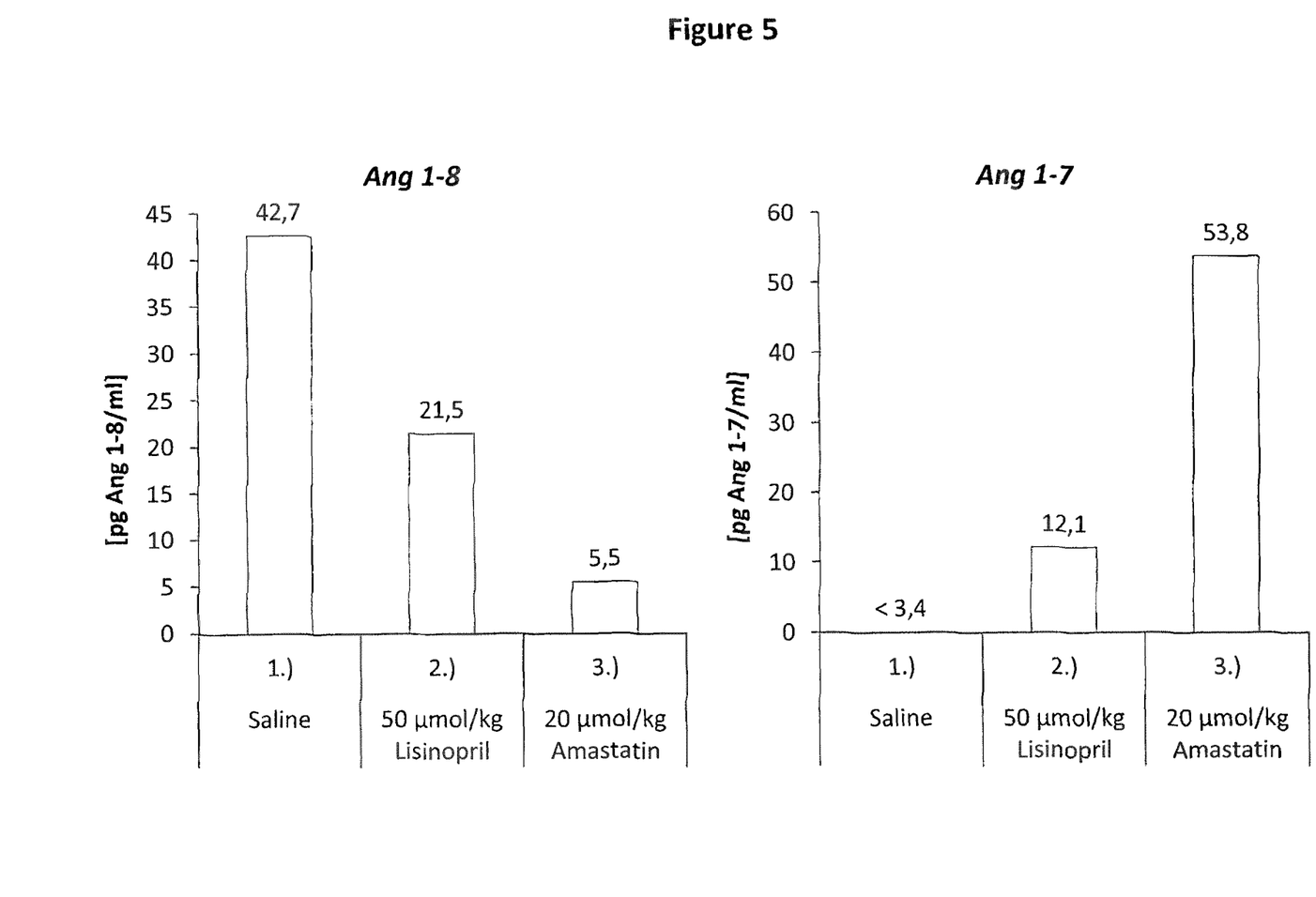

Pharmacologic effects of the sequential administration of Lisinopril and Amastatin to a male SHR rat (FIG. 5).
Methods
A male SHR rat was anesthetized by isoflurane followed by preparation of the jugular vein and insertion of an infusion catheter. At the beginning of the experiment (t=0 min) 200 µl of phosphate buffered saline was infused into the jugular vein within a period of 15 seconds. 10 min following saline infusion, 500 µl heparin blood was collected from the tail vein and placed on ice. Another 10 min later (t=20 min) a dose of 50 µmol/kg Lisinopril was in fused in a volume of 200 µl phosphate buffered saline, followed by another tail vein heparin blood collection of 500 µl heparin blood 10 min after Lisinopril infusion. Finally, 10 min following sample collection, 20 µmol/kg Amastatin was infused into the jugular vein in a volume of 200 µl phosphate buffered saline. After final sample collection (500 µl heparin blood) at 10 min after Amastatin infusion, the rat was sacrificed and organs were shock frozen in liquid nitrogen for later analysis. Heparin blood samples were equilibrated at 37° C. for 30 minutes before stabilization with a protease inhibitor cocktail suitable for stabilization of angiotensin peptides (for further reference see WO 2013/182237). Following centrifugation of blood at 2500 g for 5 min at 4° C., Ang 1-8 and Ang 1-7 was quantified in the plasma samples by LC-MS/MS analysis.
Results
10 min following infusion of saline, equilibrium Ang 1-8 levels were 42.7 pg/ml while Ang 1-7 were below the quantification limit of 3.4 pg/ml (FIG. 5). Following infusion of Lisinopril, the Ang 1-8 level was reduced to 21.5 pg/ml, while Ang 1-7 became detectable, reaching a concentration of 12.1 pg/ml. On top infusion of Amastatin resulted in a profound increase of Ang 1-7 (4.4 fold) to 53.8 pg/ml while Ang 1-8 was even further reduced to 5.5 pg/ml.

Discussion of Examples 1 to 5

As shown in FIG. 1, the combination of Amastatin and Lisinopril improves the efficiency of anti-hypertensive effects mediated by ACE inhibitors. Compared to the administration of the ACE inhibitor alone, co-administration of Amastatin in SHR rats surprisingly improved the expected blood pressure lowering effect mediated of Lisinopril by more than 67%. Interestingly, the administration of Amastatin alone resulted in a moderate (not significant, p=0.6) increase in blood pressure, suggesting an unknown mechanism to be involved in the observed physiologic effect. Amastatin is an aminopeptidase inhibitor with a broad panel of molecular targets.
Among Amastatin's targets, Aminopeptidase A (APA, EC 3.4.11.7) has been described to be involved in angiotensin metabolism. Angiotensins are peptide hormones of the Renin-Angiotensin-System (RAS), being an endocrine hormone system that is involved in blood pressure regulation and that is present in plasma, cells and virtually all tissues. Ang 1-8, the main effector peptide of the RAS is an octapeptide signaling via the AT1-Receptor (AT1R). A hyper-activated RAS and therefore increased Ang 1-8 levels are associated with increased blood pressure and a variety of cardiovascular diseases.
Aminopeptidase A is encoded by the ENPEP gene and has been described to be responsible for the degradation of Ang 1-8 in vivo and in vitro. Therefore, a blood pressure increase in response to the administration of an APA inhibitor might be expected. Surprisingly, despite resulting in increased Ang 1-8 levels in human plasma (FIG. 2, left panel), the administration of Amastatin alone to SHR rats did not have a significant impact on blood pressure in our experimental model (FIG. 1).
APA inhibitors are currently under investigation for the treatment of hypertension and have been shown to be effective in lowering blood pressure when being administered locally into the brain of rats. In contrast to the RAS in plasma, blood or other tissues ("Peripheral" or "Systemic" RAS), the brain displays physiologically important differences in angiotensin metabolism. One key feature of the local RAS in the brain ("Central" RAS) is that in contrast to the periphery, Angiotensin III (Ang 2-8) and not Ang 1-8 is thought to be responsible for increasing blood pressure. Ang 2-8 is the product of the enzymatic conversion of Ang 1-8 by APA, explaining the rational for developing a centrally active APA blocker for the treatment of hypertension.

As a consequence, this mechanism has recently been addressed by a brain targeted APA blocker (RB150) that is currently developed for the treatment of hypertension in humans (Llorens-Cortes et al., see e.g. U.S. Pat. No. 6,340, 708). Importantly, the active metabolite of RB150 (EC-33) has no effect on blood pressure when administered to the periphery by intravenous injection in rats and has to possess a high selectivity for APA over APN (at least 100-fold), which is a prerequisite for its effectiveness against hypertension via affecting central angiotensin metabolism.

In contrast to RB150, which is shown to be effective in lowering blood pressure via the inhibition of APA by its active metabolite EC-33 in the brain, the ineffectiveness of Amastatin alone in lowering blood pressure in SHR rats, the low affinity of Amastatin for APA compared to APN (Ahmad and Ward 1990, JPET), as well as the lack of inhibitory activity of active concentrations of Amastatin against APA in vitro and ex vivo (FIG. 3), point to an APA independent, peripheral phenomenon that is responsible for the improved effect of a combination of Amastatin and ACE inhibitors on blood pressure in SHR rats when compared with ACE inhibitor treatment alone (FIG. 1).

In order to elucidate the mechanisms involved in the surprising efficiency of the combination of Amastatin and Lisinopril in decreasing blood pressure in SHR rats, we investigated the pharmacologic impact of these drugs on the human RAS (Example 2). Surprisingly, the combination of Amastatin with ACE inhibitors results in a potentiation of plasma Ang 1-7 levels, while Ang 1-8 levels remained suppressed when compared to ACE inhibitor treated samples.

APA is well known to be involved in Ang 1-8 degradation. In order to test if APA inhibition by Amastatin might be responsible for the effects observed on Ang 1-8 and Ang 1-7 levels (FIG. 2) we investigated the inhibitory capacity of Amastatin on human recombinant APA in vitro and in vivo. Surprisingly, 0.1 µM Amastatin, which showed massive effects on Ang 1-8 and Ang 1-7 levels in human blood, did not affect APA activity in vitro and ex vivo, supporting the presence of an APA independent mechanism that might explain the surprising effects of the combination of Amastatin and Lisinopril on rat blood pressure and human Ang 1-8 and Ang 1-7 levels.

Ang 1-7 has been reported to represent a functional counterpart for Ang 1-8, acting via the MAS receptor and being responsible for blood pressure lowering, anti-inflammatory, anti-fibrotic and anti proliferative effects. Therefore it is in the focus of treatment developments against cardiovascular diseases and hypertension (Ferreira 2012, Expert Opin. Ther. Patents).

It is known that ACE inhibitor treatment is associated with an increase in Ang 1-7, which resulted in speculations about a concerted action of increased Ang 1-7 levels with decreased Ang 1-8 levels underlying the effectiveness of ACE inhibitors in the treatment of hypertension. The profound impact of Amastatin on Ang 1-7 levels in human plasma, which is exclusively observed when ACE inhibitors are present, is a previously unknown aspect of angiotensin metabolism and might represent the mechanism underlying the surprising effects on blood pressure observed in SHR rats (FIG. 1). Findings obtained in Example 5 support this hypothesis, as Amastatin infusion in SHR rats on top of Lisinopril results in a profound increase in Ang 1-7 levels already 10 min following intravenous administration of Amastatin. The exact molecular mechanisms explaining the results obtained in our studies are still to be further elucidated and might lead to the development a novel class of anti-hypertensive and cardiovascular drugs in the future.

The invention is further illustrated by the following embodiments, which can be readily combined with any one of embodiments 1 to 30:

1. A pharmaceutical composition comprising
   a. at least one aspartyl aminopeptidase inhibitor and at least one angiotensin-converting-enzyme (ACE) inhibitor, or
   b. at least one aspartyl aminopeptidase inhibitor and at least one chymase inhibitor.
2. The pharmaceutical composition as defined in embodiment 1 comprising at least one aspartyl aminopeptidase inhibitor and at least one angiotensin-converting-enzyme (ACE) inhibitor.
3. The pharmaceutical composition as defined in embodiment 1 or 2 comprising at least one aspartyl aminopeptidase inhibitor and at least one angiotensin-converting-enzyme (ACE) inhibitor and at least one chymase inhibitor.
4. A pharmaceutical composition possessing inhibitory activity against
   a. aspartyl aminopeptidase and angiotensin-converting-enzyme (ACE), or
   b. against aspartyl aminopeptidase and chymase.
5. The pharmaceutical composition as defined in embodiment 4 possessing inhibitory activity against aspartyl aminopeptidase and angiotensin-converting-enzyme (ACE) and chymase.
6. The pharmaceutical composition as defined in any one of the preceding embodiments for the treatment of a disease related to the Renin-Angiotensin system (RAS).
7. The pharmaceutical composition as defined in embodiment 6, wherein the disease related to the RAS is a hyperplastic disease, neoplastic disease, and/or a cardiovascular disease.
8. The pharmaceutical composition as defined in embodiment 7, wherein the cardiovascular disease is hypertension and/or heart failure.
9. The pharmaceutical composition as defined in embodiment 7, wherein the neoplastic disease is cancer.
10. The pharmaceutical composition as defined in any of the preceding embodiments, wherein
    a. the at least one aspartyl aminopeptidase inhibitor and the at least one ACE inhibitor, or
    b. the at least one aspartyl aminopeptidase inhibitor and the at least one chymase inhibitor, or
    c. the at least one aspartyl aminopeptidase inhibitor and the at least one ACE inhibitor and the at least one chymase inhibitor
    are combined in a single molecule.
11. The pharmaceutical composition as defined in any of the preceding embodiments, wherein the aspartyl aminopeptidase is DNPEP.
12. The pharmaceutical composition as defined in any of the preceding embodiments, wherein the aspartyl aminopeptidase inhibitor is not a selective aminopeptidase A inhibitor.
13. The pharmaceutical composition as defined in any of the preceding embodiments, wherein the aspartyl aminopeptidase inhibitor is Amastatin or a derivative thereof.
14. The pharmaceutical composition as defined in any one of embodiments 1 to 12, wherein the aspartyl aminopeptidase inhibitor is not Amastatin.
15. The pharmaceutical composition as defined in any of the preceding embodiments, wherein the ACE inhibitor is Lisinopril and/or Captopril.

16. The pharmaceutical composition as defined in any of the preceding embodiments, wherein the pharmacologic effect of said composition is mediated by affecting the RAS.
17. The pharmaceutical composition as defined in any of the preceding embodiments, wherein said composition is for systemic administration.
18. The pharmaceutical composition as defined in embodiment 17, wherein said composition is for oral administration.
19. A kit of parts comprising
    a. a pharmaceutical composition comprising an aspartyl aminopeptidase inhibitor and a pharmaceutical composition comprising an angiotensin-converting-enzyme (ACE) inhibitor, or
    b. a pharmaceutical composition comprising an aspartyl aminopeptidase inhibitor and a pharmaceutical composition comprising a chymase inhibitor, or
    c. a pharmaceutical composition comprising an aspartyl aminopeptidase inhibitor and a pharmaceutical composition comprising an angiotensin-converting-enzyme (ACE) inhibitor and a pharmaceutical composition comprising a chymase inhibitor.
20. The kit as defined in embodiment 19, wherein
    a. the at least one aspartyl aminopeptidase inhibitor and the at least one ACE inhibitor, or
    b. the at least one aspartyl aminopeptidase inhibitor and the at least one chymase inhibitor, or
    c. the at least one aspartyl aminopeptidase inhibitor and the at least one ACE inhibitor and the at least one chymase inhibitor
    are combined in a single molecule.
21. A method for decreasing the blood pressure in a subject by administering a therapeutically effective amount of a pharmaceutical composition as defined in any one of embodiments 1 to 18 to the subject.
22. A method for treating a disease related to the RAS in a subject by administering a therapeutically effective amount of a pharmaceutical composition as defined in any one of embodiments 1 to 18 to the subject.
23. The method as defined in embodiment 21 or 22, wherein the subject is a human.
24. The method as defined in any one of embodiments 21 to 23, wherein the disease related to the RAS is a hyperplastic disease, a neoplastic disease, and/or a cardiovascular disease.
25. The method of embodiment 24, wherein the cardiovascular disease is hypertension and/or heart failure.
26. The method of embodiment 24, wherein the neoplastic disease is cancer.
27. A method of inhibiting aspartyl aminopeptidase and in addition of inhibiting chymase and/or angiotensin-converting-enzyme (ACE) in a cell, comprising treating said cell with an aspartyl aminopeptidase inhibitor and in addition with a chymase inhibitor and/or an angiotensin-converting-enzyme (ACE) inhibitor.
28. The method of embodiment 27 wherein said cell is in a subject or not in a subject.
29. The method of embodiment 28, wherein said subject is a human or non-human animal.
30. The use of an aspartyl aminopeptidase inhibitor and further a chymase inhibitor and/or an angiotensin-converting-enzyme (ACE) inhibitor in the manufacture of a medicament for the treatment of a disease related to the Renin-Angiotensin system (RAS), preferably as defined in any one of embodiments 1 to 29.

The invention claimed is:

1. A pharmaceutical composition comprising:
   at least one aspartyl aminopeptidase inhibitor and at least one angiotensin-converting-enzyme (ACE) inhibitor; and/or
   at least one aspartyl aminopeptidase inhibitor and at least one chymase inhibitor.
2. The pharmaceutical composition of claim 1, further defined as comprising at least one aspartyl aminopeptidase inhibitor, at least one angiotensin-converting-enzyme (ACE) inhibitor, and at least one chymase inhibitor.
3. The pharmaceutical composition of claim 1,
   further defined as comprising at least one aspartyl aminopeptidase inhibitor and at least one ACE inhibitor combined in a single molecule.
4. The pharmaceutical composition of claim 1, wherein the aspartyl aminopeptidase inhibitor is not a selective aminopeptidase A inhibitor.
5. The pharmaceutical composition of claim 1, wherein the aspartyl aminopeptidase inhibitor is a selective DNPEP inhibitor.
6. The pharmaceutical composition of claim 1, wherein the aspartyl aminopeptidase inhibitor is Amastatin or a chemical derivative thereof, that inhibits an aspartyl aminopeptidase that is involved in the metabolism of Ang 1-8 and Ang 1-7.
7. The pharmaceutical composition of claim 1, wherein the aspartyl aminopeptidase inhibitor is not Amastatin.
8. The pharmaceutical composition of claim 1, wherein the ACE inhibitor is Lisinopril and/or Captopril.
9. The pharmaceutical composition of claim 1, further defined as having a pharmacologic effect that is mediated by affecting Renin-Angiotensin system (RAS).
10. The pharmaceutical composition of claim 1, wherein the composition is adapted for systemic administration.
11. The pharmaceutical composition of claim 10, wherein the composition is adapted for oral administration.
12. A method of treating a disease related to Renin-Angiotensin system (RAS) comprising:
    obtaining a pharmaceutical composition of claim 1; and
    administering the pharmaceutical composition to a subject;
    wherein a disease related to RAS is treated in the subject, and
    wherein the disease related to RAS is selected from the group consisting of a cardiovascular disease, a cancer that is characterized by an increased Ang II level and/or in which an increase in the Ang 1-7 level is advantageous, lung cancer, prostate cancer, breast cancer, osteosarcoma, pediatric sarcoma, and brain cancer.
13. The method of claim 12, wherein the cardiovascular disease is hypertension and/or heart failure.
14. The method of claim 12, wherein a pharmacologic effect of the composition is mediated by affecting the RAS.
15. The method of claim 12, wherein the composition is administered systemically.
16. The method of claim 12, wherein the composition is administered orally.
17. A kit of parts comprising:
    a pharmaceutical composition comprising an aspartyl aminopeptidase inhibitor and a pharmaceutical composition comprising an angiotensin-converting-enzyme (ACE) inhibitor; or
    a pharmaceutical composition comprising an aspartyl aminopeptidase inhibitor and a pharmaceutical composition comprising a chymase inhibitor; or
    a pharmaceutical composition comprising an aspartyl aminopeptidase inhibitor and a pharmaceutical composition comprising an angiotensin-converting-enzyme (ACE) inhibitor and a pharmaceutical composition comprising a chymase inhibitor.

18. The kit of claim 17, wherein:
the at least one aspartyl aminopeptidase inhibitor and the at least one ACE inhibitor; or
the at least one aspartyl aminopeptidase inhibitor and the at least one chymase inhibitor; or
the at least one aspartyl aminopeptidase inhibitor and the at least one ACE inhibitor and the at least one chymase inhibitor;
are combined in a single molecule.

19. The pharmaceutical composition of claim 1, further defined as comprising at least one aspartyl aminopeptidase inhibitor and at least one chymase inhibitor combined in a single molecule.

20. The pharmaceutical composition of claim 2, further defined as comprising the at least one aspartyl aminopeptidase inhibitor, the at least one angiotensin-converting-enzyme (ACE) inhibitor, and the at least one chymase inhibitor combined in a single molecule.

21. The pharmaceutical composition of claim 1, wherein the at least one aspartyl aminopeptidase inhibitor inhibits an aspartyl aminopeptidase which can cleave off one or more N-terminal amino acids of Ang 1-5, Ang1-6, Ang 1-7, Ang 1-8, Ang 1-9, and/or Ang 1-10.

22. The method of claim 12, wherein the breast cancer is triple negative breast cancer.

23. The method of claim 12, wherein the at least one aspartyl aminopeptidase inhibitor inhibits an aspartyl aminopeptidase which can cleave off one or more N-terminal amino acids of Ang 1-5, Ang1-6, Ang 1-7, Ang 1-8, Ang 1-9, and/or Ang 1-10.

* * * * *